(12) United States Patent
Kuo et al.

(10) Patent No.: US 11,612,454 B2
(45) Date of Patent: Mar. 28, 2023

(54) INDIVIDUALIZED ORTHODONTIC TREATMENT INDEX

(71) Applicant: Align Technology, Inc., San Jose, CA (US)

(72) Inventors: Eric E. Kuo, San Jose, CA (US); Vadim Matov, San Jose, CA (US); Larry Lai, San Jose, CA (US); Fuming Wu, Pleasanton, CA (US); Jihua Cheng, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 1021 days.

(21) Appl. No.: 14/967,598

(22) Filed: Dec. 14, 2015

(65) Prior Publication Data
US 2016/0095668 A1 Apr. 7, 2016

Related U.S. Application Data

(63) Continuation of application No. 12/771,472, filed on Apr. 30, 2010, now Pat. No. 9,211,166.

(51) Int. Cl.
*A61C 7/00* (2006.01)
*A61B 5/11* (2006.01)
(Continued)

(52) U.S. Cl.
CPC ............ *A61C 7/002* (2013.01); *A61B 5/1128* (2013.01); *A61B 5/7246* (2013.01); *A61C 7/00* (2013.01);
(Continued)

(58) Field of Classification Search
CPC .............................. A61C 7/002; G06T 2210/12
See application file for complete search history.

(56) References Cited

U.S. PATENT DOCUMENTS 2,171,695 A 9/1939 Harper
2,194,790 A 3/1940 Gluck
(Continued)

FOREIGN PATENT DOCUMENTS

AU 517102 B 11/1977
AU 3031677 A 11/1977
(Continued)

OTHER PUBLICATIONS

US 10,342,434 B2, 07/2019, Elbaz et al. (withdrawn)
(Continued)

*Primary Examiner* — Akash Saxena
(74) *Attorney, Agent, or Firm* — Shay Glenn LLP

(57) ABSTRACT

Embodiments are provided for using an individualized orthodontic treatment index. One method embodiment includes receiving an initial virtual dental model from a first scan of a patient's dentition, modifying the initial virtual dental model to create a target virtual dental model according to a treatment goal, assigning a number of dental references to the target virtual dental model, receiving a treatment outcome virtual dental model from a second scan of the patient's dentition, mapping the number of dental references from the target virtual dental model to a treatment outcome virtual dental model, and calculating an individualized treatment index score for the treatment outcome virtual dental model according to one or more differences between the target virtual dental model and the treatment outcome virtual dental model based on the number of dental references.

28 Claims, 6 Drawing Sheets

(51) Int. Cl.
*A61B 5/00* (2006.01)
*G06F 30/20* (2020.01)
*G06F 3/041* (2006.01)
*G16C 20/70* (2019.01)
*G16H 50/50* (2018.01)
*G16H 20/40* (2018.01)
*G16H 30/40* (2018.01)

(52) U.S. Cl.
CPC .............. *G06F 3/041* (2013.01); *G06F 30/20* (2020.01); *G16C 20/70* (2019.02); *G16H 50/50* (2018.01); *G06T 2210/12* (2013.01); *G16H 20/40* (2018.01); *G16H 30/40* (2018.01)

(56) References Cited

U.S. PATENT DOCUMENTS

| | | |
|---|---|---|
| 2,467,432 A | 4/1949 | Kesling |
| 2,531,222 A | 11/1950 | Kesling |
| 2,835,628 A | 5/1958 | Saffir |
| 3,089,487 A | 5/1963 | Enicks et al. |
| 3,092,907 A | 6/1963 | Traiger |
| 3,178,820 A | 4/1965 | Kesling |
| 3,211,143 A | 10/1965 | Grossberg |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,503,127 A | 3/1970 | Kasdin et al. |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,724,075 A | 4/1973 | Kesling |
| 3,738,005 A | 6/1973 | Cohen et al. |
| 3,797,115 A | 3/1974 | Silverman et al. |
| 3,813,781 A | 6/1974 | Forgione |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,949,477 A | 4/1976 | Cohen et al. |
| 3,950,851 A | 4/1976 | Bergersen |
| 3,955,282 A | 5/1976 | McNall |
| 3,983,628 A | 10/1976 | Acevedo |
| 4,014,096 A | 3/1977 | Dellinger |
| 4,039,653 A | 8/1977 | DeFoney et al. |
| 4,055,895 A | 11/1977 | Huge |
| 4,094,068 A | 6/1978 | Schinhammer |
| 4,117,596 A | 10/1978 | Wallshein |
| 4,129,946 A | 12/1978 | Kennedy |
| 4,134,208 A | 1/1979 | Pearlman |
| 4,139,944 A | 2/1979 | Bergersen |
| 4,179,811 A | 12/1979 | Hinz |
| 4,179,812 A | 12/1979 | White |
| 4,183,141 A | 1/1980 | Dellinger |
| 4,195,046 A | 3/1980 | Kesling |
| 4,204,325 A | 5/1980 | Kaelble |
| 4,253,828 A | 3/1981 | Coles et al. |
| 4,255,138 A | 3/1981 | Frohn |
| 4,278,087 A | 7/1981 | Theeuwes |
| 4,299,568 A | 11/1981 | Crowley |
| 4,324,546 A | 4/1982 | Heitlinger et al. |
| 4,324,547 A | 4/1982 | Arcan et al. |
| 4,348,178 A | 9/1982 | Kurz |
| 4,368,040 A | 1/1983 | Weissman |
| 4,419,992 A | 12/1983 | Chorbajian |
| 4,433,956 A | 2/1984 | Witzig |
| 4,433,960 A | 2/1984 | Garito et al. |
| 4,439,154 A | 3/1984 | Mayclin |
| 4,449,928 A | 5/1984 | von Weissenfluh |
| 4,450,150 A | 5/1984 | Sidman |
| 4,478,580 A | 10/1984 | Barrut |
| 4,500,294 A | 2/1985 | Lewis |
| 4,505,672 A | 3/1985 | Kurz |
| 4,505,673 A | 3/1985 | Yoshii |
| 4,519,386 A | 5/1985 | Sullivan |
| 4,523,908 A | 6/1985 | Drisaldi et al. |
| 4,526,540 A | 7/1985 | Dellinger |
| 4,553,936 A | 11/1985 | Wang |
| 4,575,330 A | 3/1986 | Hull |
| 4,575,805 A | 3/1986 | Moermann et al. |
| 4,591,341 A | 5/1986 | Andrews |
| 4,608,021 A | 8/1986 | Barrett |
| 4,609,349 A | 9/1986 | Cain |
| 4,611,288 A | 9/1986 | Duret et al. |
| 4,629,424 A | 12/1986 | Lauks et al. |
| 4,638,145 A | 1/1987 | Sakuma et al. |
| 4,656,860 A | 4/1987 | Orthuber et al. |
| 4,663,720 A | 5/1987 | Duret et al. |
| 4,664,626 A | 5/1987 | Kesling |
| 4,665,621 A | 5/1987 | Ackerman et al. |
| 4,676,747 A | 6/1987 | Kesling |
| 4,741,700 A | 5/1988 | Barabe |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,790,752 A | 12/1988 | Cheslak |
| 4,793,803 A | 12/1988 | Martz |
| 4,798,534 A | 1/1989 | Breads |
| 4,818,542 A | 4/1989 | De Luca et al. |
| 4,830,612 A | 5/1989 | Bergersen |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,861,268 A | 8/1989 | Garay et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,932,866 A | 6/1990 | Guis |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,968,251 A | 11/1990 | Darnell |
| 4,971,557 A | 11/1990 | Martin |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,015,183 A | 5/1991 | Fenick |
| 5,017,133 A | 5/1991 | Miura |
| 5,018,969 A | 5/1991 | Andreiko et al. |
| 5,027,281 A | 6/1991 | Rekow et al. |
| 5,035,613 A | 7/1991 | Breads et al. |
| 5,037,295 A | 8/1991 | Bergersen |
| 5,049,077 A | 9/1991 | Goldin et al. |
| 5,055,039 A | 10/1991 | Abbatte et al. |
| 5,061,839 A | 10/1991 | Matsuno et al. |
| 5,083,919 A | 1/1992 | Quach |
| 5,094,614 A | 3/1992 | Wildman |
| 5,100,316 A | 3/1992 | Wildman |
| 5,103,838 A | 4/1992 | Yousif |
| 5,114,339 A | 5/1992 | Guis |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,194,003 A | 3/1993 | Garay et al. |

(56) References Cited

U.S. PATENT DOCUMENTS

| | | | |
|---|---|---|---|
| 5,204,670 | A | 4/1993 | Stinton |
| 5,222,499 | A | 6/1993 | Allen et al. |
| 5,224,049 | A | 6/1993 | Mushabac |
| 5,238,404 | A | 8/1993 | Andreiko |
| 5,242,304 | A | 9/1993 | Truax et al. |
| 5,245,592 | A | 9/1993 | Kuemmel et al. |
| 5,273,429 | A | 12/1993 | Rekow et al. |
| 5,278,756 | A | 1/1994 | Lemchen et al. |
| 5,306,144 | A | 4/1994 | Hibst et al. |
| 5,314,335 | A | 5/1994 | Fung |
| 5,324,186 | A | 6/1994 | Bakanowski |
| 5,328,362 | A | 7/1994 | Watson et al. |
| 5,335,657 | A | 8/1994 | Terry et al. |
| 5,338,198 | A | 8/1994 | Wu et al. |
| 5,340,309 | A | 8/1994 | Robertson |
| 5,342,202 | A | 8/1994 | Deshayes |
| 5,344,315 | A | 9/1994 | Hanson |
| 5,368,478 | A * | 11/1994 | Andreiko ............... A61C 7/00 433/24 |
| 5,372,502 | A | 12/1994 | Massen et al. |
| D354,355 | S | 1/1995 | Hilgers |
| 5,382,164 | A | 1/1995 | Stern |
| 5,395,238 | A | 3/1995 | Andreiko et al. |
| 5,415,542 | A | 5/1995 | Kesling |
| 5,431,562 | A | 7/1995 | Andreiko et al. |
| 5,440,326 | A | 8/1995 | Quinn |
| 5,440,496 | A | 8/1995 | Andersson et al. |
| 5,447,432 | A | 9/1995 | Andreiko et al. |
| 5,449,703 | A | 9/1995 | Mitra et al. |
| 5,452,219 | A | 9/1995 | Dehoff et al. |
| 5,454,717 | A | 10/1995 | Andreiko et al. |
| 5,456,600 | A | 10/1995 | Andreiko et al. |
| 5,474,448 | A | 12/1995 | Andreiko et al. |
| 5,487,662 | A | 1/1996 | Kipke et al. |
| RE35,169 | E | 3/1996 | Lemchen et al. |
| 5,499,633 | A | 3/1996 | Fenton |
| 5,522,725 | A | 6/1996 | Jordan et al. |
| 5,528,735 | A | 6/1996 | Strasnick et al. |
| 5,533,895 | A | 7/1996 | Andreiko et al. |
| 5,540,732 | A | 7/1996 | Testerman |
| 5,542,842 | A | 8/1996 | Andreiko et al. |
| 5,543,780 | A | 8/1996 | McAuley et al. |
| 5,549,476 | A | 8/1996 | Stern |
| 5,562,448 | A | 10/1996 | Mushabac |
| 5,570,182 | A | 10/1996 | Nathel et al. |
| 5,575,655 | A | 11/1996 | Darnell |
| 5,583,977 | A | 12/1996 | Seidl |
| 5,587,912 | A | 12/1996 | Andersson et al. |
| 5,588,098 | A | 12/1996 | Chen et al. |
| 5,605,459 | A | 2/1997 | Kuroda et al. |
| 5,607,305 | A | 3/1997 | Andersson et al. |
| 5,614,075 | A | 3/1997 | Andre |
| 5,621,648 | A | 4/1997 | Crump |
| 5,626,537 | A | 5/1997 | Danyo et al. |
| 5,636,736 | A | 6/1997 | Jacobs et al. |
| 5,645,420 | A | 7/1997 | Bergersen |
| 5,645,421 | A | 7/1997 | Slootsky |
| 5,651,671 | A | 7/1997 | Seay et al. |
| 5,655,653 | A | 8/1997 | Chester |
| 5,659,420 | A | 8/1997 | Wakai et al. |
| 5,683,243 | A | 11/1997 | Andreiko et al. |
| 5,683,244 | A | 11/1997 | Truax |
| 5,691,539 | A | 11/1997 | Pfeiffer |
| 5,692,894 | A | 12/1997 | Schwartz et al. |
| 5,711,665 | A | 1/1998 | Adam et al. |
| 5,711,666 | A | 1/1998 | Hanson |
| 5,725,376 | A | 3/1998 | Poirier |
| 5,725,378 | A | 3/1998 | Wang |
| 5,730,151 | A | 3/1998 | Summer et al. |
| 5,737,084 | A | 4/1998 | Ishihara |
| 5,740,267 | A | 4/1998 | Echerer et al. |
| 5,742,700 | A | 4/1998 | Yoon et al. |
| 5,769,631 | A | 6/1998 | Williams |
| 5,774,425 | A | 6/1998 | Ivanov et al. |
| 5,790,242 | A | 8/1998 | Stern et al. |
| 5,799,100 | A | 8/1998 | Clarke et al. |
| 5,800,162 | A | 9/1998 | Shimodaira et al. |
| 5,800,174 | A | 9/1998 | Andersson |
| 5,813,854 | A | 9/1998 | Nikodem |
| 5,816,800 | A | 10/1998 | Brehm et al. |
| 5,818,587 | A | 10/1998 | Devaraj et al. |
| 5,823,778 | A | 10/1998 | Schmitt et al. |
| 5,848,115 | A | 12/1998 | Little et al. |
| 5,857,853 | A | 1/1999 | van Nifterick et al. |
| 5,866,058 | A | 2/1999 | Batchelder et al. |
| 5,876,199 | A | 3/1999 | Bergersen |
| 5,879,158 | A | 3/1999 | Doyle et al. |
| 5,880,961 | A | 3/1999 | Crump |
| 5,880,962 | A | 3/1999 | Andersson et al. |
| 5,882,192 | A | 3/1999 | Bergersen |
| 5,886,702 | A | 3/1999 | Migdal et al. |
| 5,890,896 | A | 4/1999 | Padial |
| 5,904,479 | A | 5/1999 | Staples |
| 5,911,576 | A | 6/1999 | Ulrich et al. |
| 5,934,288 | A | 8/1999 | Avila et al. |
| 5,957,686 | A | 9/1999 | Anthony |
| 5,964,587 | A | 10/1999 | Sato |
| 5,971,754 | A | 10/1999 | Sondhi et al. |
| 5,975,893 | A | 11/1999 | Chishti et al. |
| 5,975,906 | A | 11/1999 | Knutson |
| 5,980,246 | A | 11/1999 | Ramsay et al. |
| 5,989,023 | A | 11/1999 | Summer et al. |
| 5,993,413 | A | 11/1999 | Aaltonen et al. |
| 6,002,706 | A | 12/1999 | Staver et al. |
| 6,018,713 | A | 1/2000 | Coll et al. |
| 6,044,309 | A | 3/2000 | Honda |
| 6,049,743 | A | 4/2000 | Baba |
| 6,053,731 | A | 4/2000 | Heckenberger |
| 6,068,482 | A | 5/2000 | Snow |
| 6,070,140 | A | 5/2000 | Tran |
| 6,099,303 | A | 8/2000 | Gibbs et al. |
| 6,099,314 | A | 8/2000 | Kopelman et al. |
| 6,102,701 | A | 8/2000 | Engeron |
| 6,120,287 | A | 9/2000 | Chen |
| 6,123,544 | A | 9/2000 | Cleary |
| 6,152,731 | A | 11/2000 | Jordan et al. |
| 6,154,676 | A | 11/2000 | Levine |
| 6,183,248 | B1 | 2/2001 | Chishti et al. |
| 6,183,249 | B1 | 2/2001 | Brennan et al. |
| 6,186,780 | B1 | 2/2001 | Hibst et al. |
| 6,190,165 | B1 | 2/2001 | Andreiko et al. |
| 6,200,133 | B1 | 3/2001 | Kittelsen |
| 6,201,880 | B1 | 3/2001 | Elbaum et al. |
| 6,210,162 | B1 | 4/2001 | Chishti et al. |
| 6,212,435 | B1 | 4/2001 | Lattner et al. |
| 6,213,767 | B1 | 4/2001 | Dixon et al. |
| 6,217,334 | B1 | 4/2001 | Hultgren |
| 6,227,850 | B1 | 5/2001 | Chishti et al. |
| 6,230,142 | B1 | 5/2001 | Benigno et al. |
| 6,231,338 | B1 | 5/2001 | de Josselin de Jong et al. |
| 6,239,705 | B1 | 5/2001 | Glen |
| 6,243,601 | B1 | 6/2001 | Wist |
| 6,263,234 | B1 | 7/2001 | Engelhardt et al. |
| 6,283,761 | B1 | 9/2001 | Joao |
| 6,288,138 | B1 | 9/2001 | Yamamoto |
| 6,299,438 | B1 | 10/2001 | Sahagian et al. |
| 6,309,215 | B1 | 10/2001 | Phan et al. |
| 6,313,432 | B1 | 11/2001 | Nagata et al. |
| 6,315,553 | B1 | 11/2001 | Sachdeva et al. |
| 6,328,745 | B1 | 12/2001 | Ascherman |
| 6,332,774 | B1 | 12/2001 | Chikami |
| 6,334,073 | B1 | 12/2001 | Levine |
| 6,350,120 | B1 | 2/2002 | Sachdeva et al. |
| 6,364,660 | B1 | 4/2002 | Durbin et al. |
| 6,382,975 | B1 | 5/2002 | Poirier |
| 6,386,878 | B1 | 5/2002 | Pavlovskaia et al. |
| 6,394,802 | B1 | 5/2002 | Hahn |
| 6,402,510 | B1 | 6/2002 | Williams |
| 6,402,707 | B1 | 6/2002 | Ernst |
| 6,405,729 | B1 | 6/2002 | Thornton |
| 6,406,292 | B1 | 6/2002 | Chishti et al. |
| 6,409,504 | B1 | 6/2002 | Jones et al. |
| 6,413,086 | B1 | 7/2002 | Womack |
| 6,414,264 | B1 | 7/2002 | von Falkenhausen |

(56) References Cited

U.S. PATENT DOCUMENTS

| | | |
|---|---|---|
| 6,414,708 B1 | 7/2002 | Carmeli et al. |
| 6,435,871 B1 | 8/2002 | Inman |
| 6,436,058 B1 | 8/2002 | Krahner et al. |
| 6,441,354 B1 | 8/2002 | Seghatol et al. |
| 6,450,167 B1 | 9/2002 | David et al. |
| 6,450,807 B1 | 9/2002 | Chishti et al. |
| 6,462,301 B1 | 10/2002 | Scott et al. |
| 6,470,338 B1 | 10/2002 | Rizzo et al. |
| 6,471,511 B1 | 10/2002 | Chishti et al. |
| 6,471,512 B1 | 10/2002 | Sachdeva et al. |
| 6,471,970 B1 | 10/2002 | Fanara et al. |
| 6,482,002 B2 | 11/2002 | Jordan et al. |
| 6,482,298 B1 | 11/2002 | Bhatnagar |
| 6,496,814 B1 | 12/2002 | Busche |
| 6,496,816 B1 | 12/2002 | Thiesson et al. |
| 6,499,026 B1 | 12/2002 | Rivette et al. |
| 6,499,995 B1 | 12/2002 | Schwartz |
| 6,507,832 B1 | 1/2003 | Evans et al. |
| 6,514,074 B1 | 2/2003 | Chishti et al. |
| 6,515,593 B1 | 2/2003 | Stark et al. |
| 6,516,288 B2 | 2/2003 | Bagne |
| 6,516,805 B1 | 2/2003 | Thornton |
| 6,520,772 B2 | 2/2003 | Williams |
| 6,523,009 B1 | 2/2003 | Wilkins |
| 6,523,019 B1 | 2/2003 | Borthwick |
| 6,524,101 B1 | 2/2003 | Phan et al. |
| 6,526,168 B1 | 2/2003 | Ornes et al. |
| 6,526,982 B1 | 3/2003 | Strong |
| 6,529,891 B1 | 3/2003 | Heckerman |
| 6,529,902 B1 | 3/2003 | Kanevsky et al. |
| 6,532,455 B1 | 3/2003 | Martin et al. |
| 6,535,865 B1 | 3/2003 | Skaaning et al. |
| 6,540,512 B1 | 4/2003 | Sachdeva et al. |
| 6,540,707 B1 | 4/2003 | Stark et al. |
| 6,542,593 B1 | 4/2003 | Amuah |
| 6,542,881 B1 | 4/2003 | Meidan et al. |
| 6,542,894 B1 | 4/2003 | Lee et al. |
| 6,542,903 B2 | 4/2003 | Hull et al. |
| 6,551,243 B2 | 4/2003 | Bocionek et al. |
| 6,554,837 B1 | 4/2003 | Hauri et al. |
| 6,556,659 B1 | 4/2003 | Bowman Amuah |
| 6,556,977 B1 | 4/2003 | Lapointe et al. |
| 6,560,592 B1 | 5/2003 | Reid et al. |
| 6,564,209 B1 | 5/2003 | Dempski et al. |
| 6,567,814 B1 | 5/2003 | Bankier et al. |
| 6,571,227 B1 | 5/2003 | Agrafiotis et al. |
| 6,572,372 B1 | 6/2003 | Phan et al. |
| 6,573,998 B2 | 6/2003 | Sabban |
| 6,574,561 B2 | 6/2003 | Alexander et al. |
| 6,578,003 B1 | 6/2003 | Camarda et al. |
| 6,580,948 B2 | 6/2003 | Haupert et al. |
| 6,587,529 B1 | 7/2003 | Staszewski et al. |
| 6,587,828 B1 | 7/2003 | Sachdeva |
| 6,592,368 B1 | 7/2003 | Weathers |
| 6,594,539 B1 | 7/2003 | Geng |
| 6,595,342 B1 | 7/2003 | Maritzen et al. |
| 6,597,934 B1 | 7/2003 | de Jong et al. |
| 6,598,043 B1 | 7/2003 | Baclawski |
| 6,599,250 B1 | 7/2003 | Webb et al. |
| 6,604,527 B1 | 8/2003 | Palmisano |
| 6,606,744 B1 | 8/2003 | Mikurak |
| 6,607,382 B1 | 8/2003 | Kuo et al. |
| 6,611,783 B2 | 8/2003 | Kelly et al. |
| 6,611,867 B1 | 8/2003 | Bowman Amuah |
| 6,613,001 B1 | 9/2003 | Dworkin |
| 6,615,158 B2 | 9/2003 | Wenzel et al. |
| 6,616,447 B1 | 9/2003 | Rizoiu et al. |
| 6,616,579 B1 | 9/2003 | Reinbold et al. |
| 6,621,491 B1 | 9/2003 | Baumrind et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,626,569 B2 | 9/2003 | Reinstein et al. |
| 6,626,669 B2 | 9/2003 | Zegarelli |
| 6,633,772 B2 | 10/2003 | Ford et al. |
| 6,640,128 B2 | 10/2003 | Vilsmeier et al. |
| 6,643,646 B2 | 11/2003 | Su et al. |
| 6,647,383 B1 | 11/2003 | August et al. |
| 6,650,944 B2 | 11/2003 | Goedeke et al. |
| 6,671,818 B1 | 12/2003 | Mikurak |
| 6,675,104 B2 | 1/2004 | Paulse et al. |
| 6,678,669 B2 | 1/2004 | Lapointe et al. |
| 6,682,346 B2 | 1/2004 | Chishti et al. |
| 6,685,469 B2 | 2/2004 | Chishti et al. |
| 6,689,055 B1 | 2/2004 | Mullen et al. |
| 6,690,761 B2 | 2/2004 | Lang et al. |
| 6,691,110 B2 | 2/2004 | Wang et al. |
| 6,694,234 B2 | 2/2004 | Lockwood et al. |
| 6,697,164 B1 | 2/2004 | Babayoff et al. |
| 6,697,793 B2 | 2/2004 | McGreevy |
| 6,702,765 B2 | 3/2004 | Robbins et al. |
| 6,702,804 B1 | 3/2004 | Ritter et al. |
| 6,705,863 B2 | 3/2004 | Phan et al. |
| 6,729,876 B2 | 5/2004 | Chishti et al. |
| 6,733,289 B2 | 5/2004 | Manemann et al. |
| 6,736,638 B1 | 5/2004 | Sachdeva et al. |
| 6,739,869 B1 | 5/2004 | Taub et al. |
| 6,744,932 B1 | 6/2004 | Rubbert et al. |
| 6,749,414 B1 | 6/2004 | Hanson et al. |
| 6,769,913 B2 | 8/2004 | Hurson |
| 6,772,026 B2 | 8/2004 | Bradbury et al. |
| 6,790,036 B2 | 9/2004 | Graham |
| 6,802,713 B1 | 10/2004 | Chishti et al. |
| 6,814,574 B2 | 11/2004 | Abolfathi et al. |
| 6,830,450 B2 | 12/2004 | Knopp et al. |
| 6,832,912 B2 | 12/2004 | Mao |
| 6,832,914 B1 | 12/2004 | Bonnet et al. |
| 6,843,370 B2 | 1/2005 | Tuneberg |
| 6,845,175 B2 | 1/2005 | Kopelman et al. |
| 6,885,464 B1 | 4/2005 | Pfeiffer et al. |
| 6,890,285 B2 | 5/2005 | Rahman et al. |
| 6,951,254 B2 | 10/2005 | Morrison |
| 6,976,841 B1 | 12/2005 | Osterwalder |
| 6,978,268 B2 | 12/2005 | Thomas et al. |
| 6,983,752 B2 | 1/2006 | Garabadian |
| 6,984,128 B2 | 1/2006 | Breining et al. |
| 6,988,893 B2 | 1/2006 | Haywood |
| 7,016,952 B2 | 3/2006 | Mullen et al. |
| 7,020,963 B2 | 4/2006 | Cleary et al. |
| 7,036,514 B2 | 5/2006 | Heck |
| 7,040,896 B2 | 5/2006 | Pavlovskaia et al. |
| 7,077,647 B2 * | 7/2006 | Choi ................ A61C 7/00 433/213 |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,134,874 B2 | 11/2006 | Chishti et al. |
| 7,137,812 B2 | 11/2006 | Cleary et al. |
| 7,138,640 B1 | 11/2006 | Delgado et al. |
| 7,140,877 B2 | 11/2006 | Kaza |
| 7,142,312 B2 | 11/2006 | Quadling et al. |
| 7,155,373 B2 | 12/2006 | Jordan et al. |
| 7,156,655 B2 | 1/2007 | Sachdeva et al. |
| 7,156,661 B2 * | 1/2007 | Choi ................ A61C 7/00 433/213 |
| 7,166,063 B2 | 1/2007 | Rahman et al. |
| 7,184,150 B2 | 2/2007 | Quadling et al. |
| 7,191,451 B2 | 3/2007 | Nakagawa |
| 7,192,273 B2 | 3/2007 | McSurdy |
| 7,194,781 B1 | 3/2007 | Orjela |
| 7,217,131 B2 | 5/2007 | Vuillemot |
| 7,220,124 B2 | 5/2007 | Taub et al. |
| 7,229,282 B2 | 6/2007 | Andreiko et al. |
| 7,234,937 B2 | 6/2007 | Sachdeva et al. |
| 7,241,142 B2 | 7/2007 | Abolfathi et al. |
| 7,244,230 B2 | 7/2007 | Duggirala et al. |
| 7,245,753 B2 | 7/2007 | Squilla et al. |
| 7,257,136 B2 | 8/2007 | Mori et al. |
| 7,286,954 B2 | 10/2007 | Kopelman et al. |
| 7,292,759 B2 | 11/2007 | Boutoussov et al. |
| 7,294,141 B2 | 11/2007 | Bergersen |
| 7,302,842 B2 | 12/2007 | Biester et al. |
| 7,320,592 B2 | 1/2008 | Chishti et al. |
| 7,328,706 B2 | 2/2008 | Barach et al. |

(56) References Cited

U.S. PATENT DOCUMENTS

| | | | |
|---|---|---|---|
| 7,329,122 B1 | 2/2008 | Scott |
| 7,338,327 B2 | 3/2008 | Sticker et al. |
| D565,509 S | 4/2008 | Fechner et al. |
| 7,351,116 B2 | 4/2008 | Dold |
| 7,354,270 B2 | 4/2008 | Abolfathi et al. |
| 7,357,637 B2 | 4/2008 | Liechtung |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,476,100 B2 | 1/2009 | Kuo |
| 7,500,851 B2 | 3/2009 | Williams |
| D594,413 S | 6/2009 | Palka et al. |
| 7,543,511 B2 | 6/2009 | Kimura et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |
| 7,637,740 B2 | 12/2009 | Knopp |
| 7,641,473 B2 | 1/2010 | Sporbert et al. |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,711,447 B2 | 5/2010 | Lu et al. |
| 7,724,378 B2 | 5/2010 | Babayoff |
| D618,619 S | 6/2010 | Walter |
| 7,728,848 B2 | 6/2010 | Petrov et al. |
| 7,731,508 B2 | 6/2010 | Borst |
| 7,735,217 B2 | 6/2010 | Borst |
| 7,740,476 B2 | 6/2010 | Rubbert et al. |
| 7,744,369 B2 | 6/2010 | Imgrund et al. |
| 7,746,339 B2 | 6/2010 | Matov et al. |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,687 B2 | 10/2010 | Minagi et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,841,464 B2 | 11/2010 | Cinader et al. |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,869,983 B2 | 1/2011 | Raby et al. |
| 7,872,760 B2 | 1/2011 | Ertl |
| 7,874,836 B2 | 1/2011 | McSurdy |
| 7,874,837 B2 | 1/2011 | Chishti et al. |
| 7,874,849 B2 | 1/2011 | Sticker et al. |
| 7,878,801 B2 | 2/2011 | Abolfathi et al. |
| 7,878,805 B2 | 2/2011 | Moss et al. |
| 7,880,751 B2 | 2/2011 | Kuo et al. |
| 7,892,474 B2 | 2/2011 | Shkolnik et al. |
| 7,904,308 B2 | 3/2011 | Arnone et al. |
| 7,907,280 B2 | 3/2011 | Johs et al. |
| 7,929,151 B2 | 4/2011 | Liang et al. |
| 7,930,189 B2 | 4/2011 | Kuo |
| 7,947,508 B2 | 5/2011 | Tricca et al. |
| 7,959,308 B2 | 6/2011 | Freeman et al. |
| 7,963,766 B2 | 6/2011 | Cronauer |
| 7,970,627 B2 | 6/2011 | Kuo et al. |
| 7,985,414 B2 | 7/2011 | Knaack et al. |
| 7,986,415 B2 | 7/2011 | Thiel et al. |
| 7,987,099 B2 | 7/2011 | Kuo et al. |
| 7,991,485 B2 | 8/2011 | Zakim |
| 8,017,891 B2 | 9/2011 | Nevin |
| 8,026,916 B2 | 9/2011 | Wen |
| 8,027,709 B2 | 9/2011 | Arnone et al. |
| 8,029,277 B2 | 10/2011 | Imgrund et al. |
| 8,038,444 B2 | 10/2011 | Kitching et al. |
| 8,045,772 B2 | 10/2011 | Kosuge et al. |
| 8,054,556 B2 | 11/2011 | Chen et al. |
| 8,075,306 B2 | 12/2011 | Kitching et al. |
| 8,077,949 B2 | 12/2011 | Liang et al. |
| 8,083,556 B2 | 12/2011 | Stadler et al. |
| 8,092,215 B2 | 1/2012 | Stone-Collonge et al. |
| 8,095,383 B2 | 1/2012 | Arnone et al. |
| 8,099,268 B2 | 1/2012 | Kitching et al. |
| 8,099,305 B2 | 1/2012 | Kuo et al. |
| 8,108,189 B2 | 1/2012 | Chelnokov et al. |
| 8,118,592 B2 | 2/2012 | Tortorici |
| 8,126,025 B2 | 2/2012 | Takeda |
| 8,136,529 B2 | 3/2012 | Kelly |
| 8,144,954 B2 | 3/2012 | Quadling et al. |
| 8,152,518 B2 | 4/2012 | Kuo |
| 8,160,334 B2 | 4/2012 | Thiel et al. |
| 8,172,569 B2 | 5/2012 | Matty et al. |
| 8,197,252 B1 | 6/2012 | Harrison |
| 8,201,560 B2 | 6/2012 | Dembro |
| 8,215,312 B2 | 7/2012 | Garabadian et al. |
| 8,240,018 B2 | 8/2012 | Walter et al. |
| 8,279,450 B2 | 10/2012 | Oota et al. |
| 8,292,617 B2 | 10/2012 | Brandt et al. |
| 8,294,657 B2 | 10/2012 | Kim et al. |
| 8,296,952 B2 | 10/2012 | Greenberg |
| 8,297,286 B2 | 10/2012 | Smernoff |
| 8,306,608 B2 | 11/2012 | Mandells et al. |
| 8,314,764 B2 | 11/2012 | Kim et al. |
| 8,332,015 B2 | 12/2012 | Ertl |
| 8,354,588 B2 | 1/2013 | Sticker et al. |
| 8,401,826 B2 | 3/2013 | Cheng et al. |
| 8,419,428 B2 | 4/2013 | Lawrence |
| 8,433,083 B2 | 4/2013 | Abolfathi et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,517,726 B2 | 8/2013 | Kakavand et al. |
| 8,520,922 B2 | 8/2013 | Wang et al. |
| 8,523,565 B2 | 9/2013 | Matty et al. |
| 8,545,221 B2 | 10/2013 | Stone-Collonge et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,639,477 B2 | 1/2014 | Chelnokov et al. |
| 8,650,586 B2 | 2/2014 | Lee et al. |
| 8,738,394 B2 | 5/2014 | Kuo |
| 8,753,114 B2 | 6/2014 | Vuillemot |
| 8,768,016 B2 | 7/2014 | Pan et al. |
| 8,771,149 B2 | 7/2014 | Rahman et al. |
| 8,843,381 B2 | 9/2014 | Kuo et al. |
| 8,856,053 B2 | 10/2014 | Mah |
| 8,870,566 B2 | 10/2014 | Bergersen |
| 8,874,452 B2 | 10/2014 | Kuo |
| 8,878,905 B2 | 11/2014 | Fisker et al. |
| 8,899,976 B2 | 12/2014 | Chen et al. |
| 8,936,463 B2 | 1/2015 | Mason et al. |
| 8,944,812 B2 | 2/2015 | Kuo |
| 8,956,058 B2 | 2/2015 | Rosch |
| 8,992,216 B2 | 3/2015 | Karazivan |
| 9,004,915 B2 | 4/2015 | Moss et al. |
| 9,039,418 B1 | 5/2015 | Rubbert |
| 9,084,535 B2 | 7/2015 | Girkin et al. |
| 9,084,657 B2 | 7/2015 | Matty et al. |
| 9,144,472 B2 * | 9/2015 | Isaacson .......... A61C 7/002 |
| 9,211,166 B2 | 12/2015 | Kuo et al. |
| 9,214,014 B2 | 12/2015 | Levin |
| 9,220,580 B2 | 12/2015 | Borovinskih et al. |
| 9,241,774 B2 | 1/2016 | Li et al. |
| 9,277,972 B2 | 3/2016 | Brandt et al. |
| 9,403,238 B2 | 8/2016 | Culp |
| 9,414,897 B2 | 8/2016 | Wu et al. |

(56) References Cited

U.S. PATENT DOCUMENTS

| | | |
|---|---|---|
| 9,433,476 B2 | 9/2016 | Khardekar et al. |
| 9,463,287 B1 | 10/2016 | Lorberbaum et al. |
| 9,492,243 B2 | 11/2016 | Kuo |
| 9,566,132 B2 | 2/2017 | Stone-Collonge et al. |
| 9,589,329 B2 | 3/2017 | Levin |
| 9,675,427 B2 | 6/2017 | Kopelman |
| 9,730,769 B2 | 8/2017 | Chen et al. |
| 9,820,829 B2 | 11/2017 | Kuo |
| 9,830,688 B2 | 11/2017 | Levin |
| 9,844,421 B2 | 12/2017 | Moss et al. |
| 9,848,985 B2 | 12/2017 | Yang et al. |
| 10,123,706 B2 | 11/2018 | Elbaz et al. |
| 10,123,853 B2 | 11/2018 | Moss et al. |
| 10,154,889 B2 | 12/2018 | Chen et al. |
| 10,172,693 B2 | 1/2019 | Brandt et al. |
| 10,195,690 B2 | 2/2019 | Culp |
| 10,231,801 B2 | 3/2019 | Korytov et al. |
| 10,238,472 B2 | 3/2019 | Levin |
| 10,248,883 B2 | 4/2019 | Borovinskih et al. |
| 10,258,432 B2 | 4/2019 | Webber |
| 10,275,862 B2 | 4/2019 | Levin |
| 10,342,638 B2 * | 7/2019 | Kitching ............... A61C 7/00 |
| 10,758,322 B2 * | 9/2020 | Pokotilov ............. A61C 7/08 |
| 10,952,817 B1 * | 3/2021 | Raslambekov ....... A61C 7/002 |
| 10,993,782 B1 * | 5/2021 | Raslambekov ....... A61C 7/002 |
| 11,109,945 B2 * | 9/2021 | Salah .................. A61C 7/002 |
| 11,278,377 B1 * | 3/2022 | Raslambekov ....... A61C 7/002 |
| 2001/0002310 A1 | 5/2001 | Chishti et al. |
| 2001/0032100 A1 | 10/2001 | Mahmud et al. |
| 2001/0038705 A1 * | 11/2001 | Rubbert ............... A61C 7/00 |
| | | 382/128 |
| 2001/0041320 A1 | 11/2001 | Phan et al. |
| 2002/0004727 A1 | 1/2002 | Knaus et al. |
| 2002/0007284 A1 | 1/2002 | Schurenberg et al. |
| 2002/0010568 A1 * | 1/2002 | Rubbert ............... A61C 7/00 |
| | | 703/6 |
| 2002/0015934 A1 | 2/2002 | Rubbert et al. |
| 2002/0025503 A1 | 2/2002 | Chapoulaud et al. |
| 2002/0026105 A1 | 2/2002 | Drazen |
| 2002/0028417 A1 | 3/2002 | Chapoulaud et al. |
| 2002/0035572 A1 | 3/2002 | Takatori et al. |
| 2002/0042038 A1 | 4/2002 | Miller et al. |
| 2002/0064752 A1 | 5/2002 | Durbin et al. |
| 2002/0064759 A1 | 5/2002 | Durbin et al. |
| 2002/0072027 A1 * | 6/2002 | Chishti ............... A61C 7/00 |
| | | 433/24 |
| 2002/0087551 A1 | 7/2002 | Hickey et al. |
| 2002/0107853 A1 | 8/2002 | Hofmann et al. |
| 2002/0156652 A1 * | 10/2002 | Sachdeva ........... A61C 9/0053 |
| | | 705/2 |
| 2002/0188478 A1 | 12/2002 | Breeland et al. |
| 2002/0192617 A1 | 12/2002 | Phan et al. |
| 2003/0000927 A1 | 1/2003 | Kanaya et al. |
| 2003/0008259 A1 | 1/2003 | Kuo et al. |
| 2003/0009252 A1 | 1/2003 | Pavlovskaia et al. |
| 2003/0019848 A1 | 1/2003 | Nicholas et al. |
| 2003/0021453 A1 | 1/2003 | Weise et al. |
| 2003/0035061 A1 | 2/2003 | Iwaki et al. |
| 2003/0049581 A1 | 3/2003 | Deluke |
| 2003/0057192 A1 | 3/2003 | Patel |
| 2003/0059736 A1 | 3/2003 | Lai et al. |
| 2003/0060532 A1 | 3/2003 | Subelka et al. |
| 2003/0068598 A1 | 4/2003 | Vallittu et al. |
| 2003/0095697 A1 | 5/2003 | Wood et al. |
| 2003/0101079 A1 | 5/2003 | McLaughlin |
| 2003/0103060 A1 | 6/2003 | Anderson et al. |
| 2003/0120517 A1 | 6/2003 | Eida et al. |
| 2003/0129565 A1 * | 7/2003 | Kaza .................. A61C 7/002 |
| | | 433/213 |
| 2003/0139834 A1 | 7/2003 | Nikolskiy et al. |
| 2003/0144886 A1 | 7/2003 | Taira |
| 2003/0172043 A1 | 9/2003 | Guyon et al. |
| 2003/0190575 A1 | 10/2003 | Hilliard |
| 2003/0192867 A1 | 10/2003 | Yamazaki et al. |
| 2003/0207224 A1 | 11/2003 | Lotte |
| 2003/0211440 A1 | 11/2003 | Kuo et al. |
| 2003/0215764 A1 | 11/2003 | Kopelman et al. |
| 2003/0224311 A1 | 12/2003 | Cronauer |
| 2003/0224313 A1 | 12/2003 | Bergersen |
| 2003/0224314 A1 | 12/2003 | Bergersen |
| 2004/0002873 A1 | 1/2004 | Sachdeva |
| 2004/0009449 A1 | 1/2004 | Mah et al. |
| 2004/0013994 A1 | 1/2004 | Goldberg et al. |
| 2004/0019262 A1 | 1/2004 | Perelgut |
| 2004/0029078 A1 | 2/2004 | Marshall |
| 2004/0038168 A1 | 2/2004 | Choi et al. |
| 2004/0054304 A1 | 3/2004 | Raby |
| 2004/0054358 A1 | 3/2004 | Cox et al. |
| 2004/0058295 A1 | 3/2004 | Bergersen |
| 2004/0068199 A1 | 4/2004 | Echauz et al. |
| 2004/0078222 A1 | 4/2004 | Khan et al. |
| 2004/0080621 A1 | 4/2004 | Fisher et al. |
| 2004/0094165 A1 | 5/2004 | Cook |
| 2004/0107118 A1 | 6/2004 | Harnsberger et al. |
| 2004/0133083 A1 | 7/2004 | Comaniciu et al. |
| 2004/0152036 A1 | 8/2004 | Abolfathi |
| 2004/0158194 A1 | 8/2004 | Wolff et al. |
| 2004/0166463 A1 | 8/2004 | Wen et al. |
| 2004/0167646 A1 | 8/2004 | Jelonek et al. |
| 2004/0170941 A1 | 9/2004 | Phan et al. |
| 2004/0193036 A1 | 9/2004 | Zhou et al. |
| 2004/0197728 A1 | 10/2004 | Abolfathi et al. |
| 2004/0214128 A1 | 10/2004 | Sachdeva et al. |
| 2004/0219479 A1 | 11/2004 | Malin et al. |
| 2004/0220691 A1 | 11/2004 | Hofmeister et al. |
| 2004/0229185 A1 | 11/2004 | Knopp |
| 2004/0259049 A1 | 12/2004 | Kopelman et al. |
| 2005/0003318 A1 | 1/2005 | Choi et al. |
| 2005/0019721 A1 | 1/2005 | Chishti |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0038669 A1 | 2/2005 | Sachdeva et al. |
| 2005/0040551 A1 | 2/2005 | Biegler et al. |
| 2005/0042569 A1 | 2/2005 | Plan et al. |
| 2005/0042577 A1 | 2/2005 | Kvitrud et al. |
| 2005/0048433 A1 | 3/2005 | Hilliard |
| 2005/0074717 A1 | 4/2005 | Cleary et al. |
| 2005/0089822 A1 | 4/2005 | Geng |
| 2005/0100333 A1 | 5/2005 | Kerschbaumer et al. |
| 2005/0108052 A1 | 5/2005 | Omaboe |
| 2005/0131738 A1 | 6/2005 | Morris |
| 2005/0144150 A1 | 6/2005 | Ramamurthy et al. |
| 2005/0171594 A1 | 8/2005 | Machan et al. |
| 2005/0171630 A1 | 8/2005 | Dinauer et al. |
| 2005/0181333 A1 | 8/2005 | Karazivan et al. |
| 2005/0186524 A1 | 8/2005 | Abolfathi et al. |
| 2005/0186526 A1 | 8/2005 | Stewart et al. |
| 2005/0216314 A1 | 9/2005 | Secor |
| 2005/0233276 A1 | 10/2005 | Kopelman et al. |
| 2005/0239013 A1 | 10/2005 | Sachdeva |
| 2005/0244781 A1 | 11/2005 | Abels et al. |
| 2005/0244791 A1 | 11/2005 | Davis et al. |
| 2005/0271996 A1 | 12/2005 | Sporbert et al. |
| 2006/0056670 A1 | 3/2006 | Hamadeh |
| 2006/0057533 A1 | 3/2006 | McGann |
| 2006/0063135 A1 | 3/2006 | Mehl |
| 2006/0078842 A1 | 4/2006 | Sachdeva et al. |
| 2006/0084024 A1 | 4/2006 | Farrell |
| 2006/0093982 A1 | 5/2006 | Wen |
| 2006/0098007 A1 | 5/2006 | Rouet et al. |
| 2006/0099545 A1 | 5/2006 | Lia et al. |
| 2006/0099546 A1 | 5/2006 | Bergersen |
| 2006/0110698 A1 | 5/2006 | Robson |
| 2006/0111631 A1 | 5/2006 | Kelliher et al. |
| 2006/0115782 A1 | 6/2006 | Li et al. |
| 2006/0115785 A1 | 6/2006 | Li et al. |
| 2006/0137813 A1 | 6/2006 | Robrecht et al. |
| 2006/0147872 A1 | 7/2006 | Andreiko |
| 2006/0154198 A1 | 7/2006 | Durbin et al. |
| 2006/0154207 A1 | 7/2006 | Kuo |
| 2006/0173715 A1 | 8/2006 | Wang |
| 2006/0183082 A1 | 8/2006 | Quadling et al. |

(56) References Cited

U.S. PATENT DOCUMENTS

| | | |
|---|---|---|
| 2006/0188834 A1 | 8/2006 | Hilliard |
| 2006/0188848 A1 | 8/2006 | Tricca et al. |
| 2006/0194163 A1 | 8/2006 | Tricca et al. |
| 2006/0199153 A1 | 9/2006 | Liu et al. |
| 2006/0204078 A1 | 9/2006 | Orth et al. |
| 2006/0223022 A1 | 10/2006 | Solomon |
| 2006/0223023 A1 | 10/2006 | Lai et al. |
| 2006/0223032 A1 | 10/2006 | Fried et al. |
| 2006/0223342 A1 | 10/2006 | Borst et al. |
| 2006/0234179 A1 | 10/2006 | Wen et al. |
| 2006/0257815 A1 | 11/2006 | De Dominicis |
| 2006/0275729 A1 | 12/2006 | Fornoff |
| 2006/0275731 A1 | 12/2006 | Wen et al. |
| 2006/0275736 A1 | 12/2006 | Wen et al. |
| 2006/0277075 A1 | 12/2006 | Salwan |
| 2006/0290693 A1 | 12/2006 | Zhou et al. |
| 2006/0292520 A1 | 12/2006 | Dillon et al. |
| 2007/0003907 A1 | 1/2007 | Chishti et al. |
| 2007/0031775 A1 | 2/2007 | Andreiko |
| 2007/0046865 A1 | 3/2007 | Umeda et al. |
| 2007/0053048 A1 | 3/2007 | Kumar et al. |
| 2007/0054237 A1 | 3/2007 | Neuschafer |
| 2007/0065768 A1 | 3/2007 | Nadav |
| 2007/0081951 A1* | 4/2007 | Stookey ............ A61K 8/4926 424/49 |
| 2007/0087300 A1 | 4/2007 | Willison et al. |
| 2007/0087302 A1 | 4/2007 | Reising et al. |
| 2007/0106138 A1 | 5/2007 | Beiski et al. |
| 2007/0122592 A1 | 5/2007 | Anderson et al. |
| 2007/0128574 A1 | 6/2007 | Kuo et al. |
| 2007/0141525 A1 | 6/2007 | Cinader |
| 2007/0141526 A1 | 6/2007 | Eisenberg et al. |
| 2007/0143135 A1 | 6/2007 | Lindquist et al. |
| 2007/0168152 A1 | 7/2007 | Matov et al. |
| 2007/0172112 A1 | 7/2007 | Paley et al. |
| 2007/0172291 A1 | 7/2007 | Yokoyama |
| 2007/0178420 A1 | 8/2007 | Keski-Nisula |
| 2007/0183633 A1 | 8/2007 | Hoffmann |
| 2007/0184402 A1 | 8/2007 | Boutoussov et al. |
| 2007/0184411 A1* | 8/2007 | Stapleton ............ A61C 19/04 433/215 |
| 2007/0185732 A1 | 8/2007 | Hicks |
| 2007/0192137 A1 | 8/2007 | Ombrellaro |
| 2007/0199929 A1 | 8/2007 | Rippl et al. |
| 2007/0207434 A1 | 9/2007 | Kuo et al. |
| 2007/0215582 A1 | 9/2007 | Roeper et al. |
| 2007/0218422 A1 | 9/2007 | Ehrenfeld |
| 2007/0231765 A1 | 10/2007 | Phan et al. |
| 2007/0238065 A1 | 10/2007 | Sherwood et al. |
| 2007/0239488 A1 | 10/2007 | DeRosso |
| 2007/0263226 A1 | 11/2007 | Kurtz et al. |
| 2008/0013727 A1 | 1/2008 | Uemura |
| 2008/0020350 A1 | 1/2008 | Matov et al. |
| 2008/0045053 A1 | 2/2008 | Stadler et al. |
| 2008/0057461 A1 | 3/2008 | Cheng et al. |
| 2008/0057467 A1 | 3/2008 | Gittelson |
| 2008/0057479 A1 | 3/2008 | Grenness |
| 2008/0059238 A1 | 3/2008 | Park et al. |
| 2008/0090208 A1 | 4/2008 | Rubbert |
| 2008/0094389 A1 | 4/2008 | Rouet et al. |
| 2008/0113317 A1 | 5/2008 | Kemp et al. |
| 2008/0115791 A1 | 5/2008 | Heine |
| 2008/0118882 A1 | 5/2008 | Su |
| 2008/0118886 A1 | 5/2008 | Liang et al. |
| 2008/0141534 A1 | 6/2008 | Hilliard |
| 2008/0169122 A1 | 7/2008 | Shiraishi et al. |
| 2008/0171934 A1 | 7/2008 | Greenan et al. |
| 2008/0176448 A1 | 7/2008 | Muller et al. |
| 2008/0182220 A1 | 7/2008 | Chishti et al. |
| 2008/0233530 A1 | 9/2008 | Cinader |
| 2008/0242144 A1 | 10/2008 | Dietz |
| 2008/0248443 A1 | 10/2008 | Chishti et al. |
| 2008/0254403 A1 | 10/2008 | Hilliard |
| 2008/0268400 A1 | 10/2008 | Moss et al. |
| 2008/0305451 A1* | 12/2008 | Kitching ............ A61C 7/00 433/24 |
| 2008/0305454 A1* | 12/2008 | Kitching ............ A61C 7/00 433/24 |
| 2008/0306724 A1 | 12/2008 | Kitching et al. |
| 2009/0029310 A1 | 1/2009 | Pumphrey et al. |
| 2009/0030290 A1 | 1/2009 | Kozuch et al. |
| 2009/0030347 A1 | 1/2009 | Cao |
| 2009/0034811 A1 | 2/2009 | Kuo |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kumada et al. |
| 2009/0087050 A1 | 4/2009 | Gandyra |
| 2009/0098502 A1 | 4/2009 | Andreiko |
| 2009/0099445 A1 | 4/2009 | Burger |
| 2009/0103579 A1 | 4/2009 | Ushimaru et al. |
| 2009/0105523 A1 | 4/2009 | Kassayan et al. |
| 2009/0130620 A1 | 5/2009 | Yazdi et al. |
| 2009/0136890 A1 | 5/2009 | Kang et al. |
| 2009/0136893 A1 | 5/2009 | Zegarelli |
| 2009/0148809 A1 | 6/2009 | Kuo et al. |
| 2009/0170050 A1 | 7/2009 | Marcus |
| 2009/0181346 A1 | 7/2009 | Orth |
| 2009/0191502 A1 | 7/2009 | Cao et al. |
| 2009/0191503 A1 | 7/2009 | Matov et al. |
| 2009/0210032 A1 | 8/2009 | Beiski et al. |
| 2009/0218514 A1 | 9/2009 | Klunder et al. |
| 2009/0281433 A1 | 11/2009 | Saadat et al. |
| 2009/0286195 A1 | 11/2009 | Sears et al. |
| 2009/0298017 A1 | 12/2009 | Boerjes et al. |
| 2009/0305540 A1 | 12/2009 | Stadler et al. |
| 2009/0316966 A1* | 12/2009 | Marshall ............ A61B 6/5217 382/128 |
| 2009/0317757 A1 | 12/2009 | Lemchen |
| 2010/0015565 A1 | 1/2010 | Carrillo Gonzalez et al. |
| 2010/0019170 A1 | 1/2010 | Hart et al. |
| 2010/0028825 A1 | 2/2010 | Lemchen |
| 2010/0045902 A1 | 2/2010 | Ikeda et al. |
| 2010/0062394 A1 | 3/2010 | Jones et al. |
| 2010/0068676 A1 | 3/2010 | Mason et al. |
| 2010/0138025 A1 | 6/2010 | Morton et al. |
| 2010/0142789 A1 | 6/2010 | Chang et al. |
| 2010/0145664 A1 | 6/2010 | Hultgren et al. |
| 2010/0145898 A1 | 6/2010 | Malfliet et al. |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0179789 A1 | 7/2010 | Sachdeva et al. |
| 2010/0193482 A1 | 8/2010 | Ow et al. |
| 2010/0196837 A1 | 8/2010 | Farrell |
| 2010/0216085 A1 | 8/2010 | Kopelman |
| 2010/0217130 A1 | 8/2010 | Weinlaender |
| 2010/0231577 A1 | 9/2010 | Kim et al. |
| 2010/0268363 A1 | 10/2010 | Karim et al. |
| 2010/0268515 A1 | 10/2010 | Vogt et al. |
| 2010/0279243 A1 | 11/2010 | Cinader et al. |
| 2010/0280798 A1 | 11/2010 | Pattijn |
| 2010/0281370 A1 | 11/2010 | Rohaly et al. |
| 2010/0303316 A1 | 12/2010 | Bullis et al. |
| 2010/0312484 A1 | 12/2010 | DuHamel et al. |
| 2010/0327461 A1 | 12/2010 | Co et al. |
| 2011/0007920 A1 | 1/2011 | Abolfathi et al. |
| 2011/0012901 A1 | 1/2011 | Kaplanyan |
| 2011/0045428 A1 | 2/2011 | Boltunov et al. |
| 2011/0056350 A1 | 3/2011 | Gale et al. |
| 2011/0065060 A1 | 3/2011 | Teixeira et al. |
| 2011/0081625 A1 | 4/2011 | Fuh |
| 2011/0091832 A1 | 4/2011 | Kim et al. |
| 2011/0102549 A1 | 5/2011 | Takahashi |
| 2011/0102566 A1 | 5/2011 | Zakian et al. |
| 2011/0104630 A1 | 5/2011 | Matov et al. |
| 2011/0136072 A1 | 6/2011 | Li et al. |
| 2011/0136090 A1 | 6/2011 | Kazemi |
| 2011/0143300 A1 | 6/2011 | Villaalba |
| 2011/0143673 A1 | 6/2011 | Landesman et al. |
| 2011/0159452 A1 | 6/2011 | Huang |
| 2011/0164810 A1 | 7/2011 | Zang et al. |
| 2011/0207072 A1 | 8/2011 | Schiemann |

(56) References Cited

U.S. PATENT DOCUMENTS

| | | |
|---|---|---|
| 2011/0212420 A1 | 9/2011 | Vuillemot |
| 2011/0220623 A1 | 9/2011 | Beutler |
| 2011/0235045 A1 | 9/2011 | Koerner et al. |
| 2011/0270588 A1* | 11/2011 | Kuo ............ A61C 7/00 703/2 |
| 2012/0040311 A1 | 2/2012 | Nilsson |
| 2012/0064477 A1 | 3/2012 | Schmitt |
| 2012/0129117 A1 | 5/2012 | McCance |
| 2012/0147912 A1 | 6/2012 | Moench et al. |
| 2012/0150494 A1 | 6/2012 | Anderson et al. |
| 2012/0166213 A1 | 6/2012 | Arnone et al. |
| 2012/0281293 A1 | 11/2012 | Gronenborn et al. |
| 2012/0322025 A1 | 12/2012 | Ozawa et al. |
| 2013/0029284 A1 | 1/2013 | Teasdale |
| 2013/0103176 A1 | 4/2013 | Kopelman et al. |
| 2013/0266326 A1 | 10/2013 | Joseph et al. |
| 2014/0081091 A1 | 3/2014 | Abolfathi et al. |
| 2014/0136222 A1 | 5/2014 | Arnone et al. |
| 2014/0142902 A1 | 5/2014 | Chelnokov et al. |
| 2014/0200863 A1* | 7/2014 | Kamat ............ G06T 19/00 703/1 |
| 2014/0280376 A1 | 9/2014 | Kuo |
| 2015/0004553 A1 | 1/2015 | Li et al. |
| 2015/0132708 A1 | 5/2015 | Kuo |
| 2015/0173856 A1 | 6/2015 | Lowe et al. |
| 2015/0238283 A1 | 8/2015 | Tanugula et al. |
| 2015/0269776 A1* | 9/2015 | Jesenko ............ G06T 17/10 345/420 |
| 2015/0320320 A1 | 11/2015 | Kopelman et al. |
| 2015/0320532 A1 | 11/2015 | Matty et al. |
| 2016/0003610 A1 | 1/2016 | Lampert et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0095668 A1* | 4/2016 | Kuo ............ A61C 7/00 703/6 |
| 2016/0106520 A1 | 4/2016 | Borovinskih et al. |
| 2016/0120621 A1 | 5/2016 | Li et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0302885 A1 | 10/2016 | Matov |
| 2016/0338799 A1 | 11/2016 | Wu et al. |
| 2016/0367339 A1 | 12/2016 | Khardekar et al. |
| 2017/0007366 A1 | 1/2017 | Kopelman et al. |
| 2017/0007367 A1 | 1/2017 | Li et al. |
| 2017/0007368 A1 | 1/2017 | Boronkay |
| 2017/0020633 A1 | 1/2017 | Stone-Collonge et al. |
| 2017/0071705 A1 | 3/2017 | Kuo |
| 2017/0100212 A1 | 4/2017 | Sherwood et al. |
| 2017/0100213 A1 | 4/2017 | Kuo |
| 2017/0105815 A1 | 4/2017 | Matov et al. |
| 2017/0128161 A1* | 5/2017 | See ............ A61C 7/002 |
| 2017/0135792 A1 | 5/2017 | Webber |
| 2017/0135793 A1 | 5/2017 | Webber et al. |
| 2017/0156821 A1 | 6/2017 | Kopelman et al. |
| 2017/0165032 A1 | 6/2017 | Webber et al. |
| 2017/0258555 A1 | 9/2017 | Kopelman |
| 2017/0319296 A1 | 11/2017 | Webber et al. |
| 2018/0000563 A1 | 1/2018 | Shanjani et al. |
| 2018/0000565 A1 | 1/2018 | Shanjani et al. |
| 2018/0028064 A1 | 2/2018 | Elbaz et al. |
| 2018/0055602 A1 | 3/2018 | Kopelman et al. |
| 2018/0071055 A1 | 3/2018 | Kuo |
| 2018/0125610 A1 | 5/2018 | Carrier et al. |
| 2018/0153648 A1 | 6/2018 | Shanjani et al. |
| 2018/0153649 A1 | 6/2018 | Wu et al. |
| 2018/0153733 A1 | 6/2018 | Kuo |
| 2018/0168788 A1 | 6/2018 | Fernie |
| 2018/0192877 A1 | 7/2018 | Atiya et al. |
| 2018/0228359 A1 | 8/2018 | Meyer et al. |
| 2018/0280118 A1 | 10/2018 | Cramer |
| 2018/0284727 A1 | 10/2018 | Cramer et al. |
| 2018/0318043 A1 | 11/2018 | Li et al. |
| 2018/0344430 A1* | 12/2018 | Salah ............ G06T 17/00 |
| 2018/0353264 A1 | 12/2018 | Riley et al. |
| 2018/0360567 A1 | 12/2018 | Xue et al. |
| 2018/0368944 A1 | 12/2018 | Sato et al. |
| 2018/0368961 A1 | 12/2018 | Shanjani et al. |
| 2019/0019187 A1 | 1/2019 | Miller et al. |
| 2019/0021817 A1 | 1/2019 | Sato et al. |
| 2019/0029522 A1 | 1/2019 | Sato et al. |
| 2019/0029784 A1 | 1/2019 | Moalem et al. |
| 2019/0046296 A1 | 2/2019 | Kopelman et al. |
| 2019/0046297 A1 | 2/2019 | Kopelman et al. |
| 2019/0069975 A1 | 3/2019 | Cam et al. |
| 2019/0076026 A1 | 3/2019 | Elbaz et al. |
| 2019/0076214 A1 | 3/2019 | Nyukhtikov et al. |
| 2019/0076216 A1 | 3/2019 | Moss et al. |
| 2019/0090983 A1 | 3/2019 | Webber et al. |
| 2019/0095539 A1 | 3/2019 | Elbaz et al. |
| 2019/0099129 A1 | 4/2019 | Kopelman et al. |
| 2019/0105130 A1 | 4/2019 | Grove et al. |
| 2019/0125494 A1 | 5/2019 | Li et al. |
| 2019/0152152 A1 | 5/2019 | O'Leary et al. |
| 2019/0160590 A1 | 5/2019 | Culp |
| 2019/0017530 A1 | 6/2019 | Morton et al. |
| 2019/0171618 A1 | 6/2019 | Kou |
| 2019/0175303 A1 | 6/2019 | Akopov et al. |
| 2019/0183614 A1 | 6/2019 | Levin |
| 2021/0045843 A1* | 2/2021 | Pokotilov ............ A61C 7/08 |

FOREIGN PATENT DOCUMENTS

| | | |
|---|---|---|
| CA | 1121955 A1 | 4/1982 |
| CN | 1655732 A | 8/2005 |
| CN | 1655733 A | 8/2005 |
| CN | 1867317 A | 11/2006 |
| CN | 102017658 A | 4/2011 |
| DE | 2749802 A1 | 5/1978 |
| DE | 3526198 A1 | 2/1986 |
| DE | 4207169 A1 | 9/1993 |
| DE | 69327661 T2 | 7/2000 |
| DE | 102005043627 A1 | 3/2007 |
| EP | 0428152 A1 | 5/1991 |
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 1989764 B1 | 7/2012 |
| EP | 2332221 B1 | 11/2012 |
| ES | 463897 A1 | 1/1980 |
| FR | 2369828 A1 | 6/1978 |
| FR | 2867377 A1 | 9/2005 |
| FR | 2930334 A1 | 10/2009 |
| GB | 1550777 A | 8/1979 |
| JP | 53-058191 A | 5/1978 |
| JP | 04-028359 A | 1/1992 |
| JP | 08-508174 A | 9/1996 |
| JP | 09-19443 A | 1/1997 |
| JP | 2003245289 A | 9/2003 |
| JP | 2000339468 A | 9/2004 |
| JP | 2005527320 A | 9/2005 |
| JP | 2005527321 A | 9/2005 |
| JP | 2006043121 A | 2/2006 |
| JP | 2007151614 A | 6/2007 |
| JP | 2007260158 A | 10/2007 |
| JP | 2007537824 A | 12/2007 |
| JP | 2008067732 A | 3/2008 |
| JP | 2008523370 A | 7/2008 |
| JP | 04184427 B1 | 11/2008 |
| JP | 2009000412 A | 1/2009 |
| JP | 2009018173 A | 1/2009 |
| JP | 2009078133 A | 4/2009 |
| JP | 2009101386 A | 5/2009 |
| JP | 2009205330 A | 9/2009 |
| JP | 2010017726 A | 1/2010 |
| JP | 2011087733 A | 5/2011 |
| KR | 10-20020062793 A | 7/2002 |

(56) References Cited

FOREIGN PATENT DOCUMENTS

| | | |
|---|---|---|
| KR | 10-20070108019 A | 11/2007 |
| KR | 10-20090065778 A | 6/2009 |
| TW | 480166 B | 3/2002 |
| WO | WO91/004713 A1 | 4/1991 |
| WO | WO92/03102 A1 | 3/1992 |
| WO | WO94/010935 A1 | 5/1994 |
| WO | WO96/23452 A1 | 8/1996 |
| WO | WO98/032394 A1 | 7/1998 |
| WO | WO98/044865 A1 | 10/1998 |
| WO | WO01/08592 A1 | 2/2001 |
| WO | WO01/85047 A2 | 11/2001 |
| WO | WO02/017776 A2 | 3/2002 |
| WO | WO02/024100 A1 | 3/2002 |
| WO | WO02/058583 A1 | 8/2002 |
| WO | WO02/062252 A1 | 8/2002 |
| WO | WO02/095475 A1 | 11/2002 |
| WO | WO03/003932 A2 | 1/2003 |
| WO | WO2005/114183 A1 | 12/2005 |
| WO | WO2006/096558 A2 | 9/2006 |
| WO | WO2006/100700 A1 | 9/2006 |
| WO | WO2006/133548 A1 | 12/2006 |
| WO | WO2007/019709 A2 | 2/2007 |
| WO | WO2007/071341 A1 | 6/2007 |
| WO | WO2007/103377 A2 | 9/2007 |
| WO | WO2008/115654 A1 | 9/2008 |
| WO | WO2009/016645 A2 | 2/2009 |
| WO | WO2009/085752 A2 | 7/2009 |
| WO | WO2009/089129 A1 | 7/2009 |
| WO | WO2009/146788 A1 | 12/2009 |
| WO | WO2009/146789 A1 | 12/2009 |
| WO | WO2010/059988 A1 | 5/2010 |
| WO | WO2010/123892 A2 | 10/2010 |

OTHER PUBLICATIONS

Iterative closest point (ICP) Wikipedia definition, https://en.wikipedia.org/wiki/Iterative_closest_point, pp. 3 (Year: 2018).*

Mariam Webster Definition of Interproximal—1 pg. (https://www.merriam-webster.com/dictionary/interproximal) (Year: 2020).*

Besl, Paul J., et al. "A Method for Registration of 3-D Shapes". IEEE Transactions on Pattern Analysis . . . vol. 14, No. 2, Feb. 1992, pp. 239-256.

Bookstein, Fred L. "Principal Warps: Thin-Plate Splines and the Decomposition of Deformations". IEEE Transactions on Pattern Analysis . . . vol. 11, No. 6, Jun. 1989, pp. 567-585.

Cangialosi, Thomas J., et al. "The ABO discrepancy index: A measure of case complexity". Am. Journal of Orthodontics . . . , Mar. 2004, pp. 270-278.

Daniels, Charles D., et al. "The Decelopment of the Index of Complexity, Outcome and Need (ICON)" J. of Orthodontics, vol. 27, 2000, pp. 149-162.

Gottschalk, S., et al. "OBBTree: A Hierarchical Structure for Rapid Interference Detection", http:..www.cs.unc.edu/~-geom/OBB/OBBT.html, 12 pgs.

AADR. American Association for Dental Research; Summary of Activities; Los Angeles, CA; p. 195; Mar. 20-23,(year of pub. sufficiently earlier than effective US filing date and any foreign priority date) 1980.

Alcaniz et al; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.

Alexander et al.; The DigiGraph Work Station Part 2 Clinical Management; J. Clin. Orthod.; pp. 402-407; (Author Manuscript); Jul. 1990.

Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.

Allesee Orthodontic Appliance: Important Tip About Wearing the Red White & Blue Active Clear Retainer System; Allesee Orthodontic Appliances—Pro Lab; 1 page; (year of pub. sufficiently earlier than effective US filing date and any foreign priority date); 1998.

Allesee Orthodontic Appliances: DuraClearTM; Product information; 1 page; (year of pub. sufficiently earlier than effective US filing date and any foreign priority date) 1997.

Allesee Orthodontic Appliances; The Choice Is Clear: Red, White & Blue . . . The Simple, Affordable, No-Braces Treatment; ( product information for doctors); retrieved from the internet (http://ormco.com/aoa/appliancesservices/RWB/doctorhtml); 5 pages on May 19, 2003.

Allesee Orthodontic Appliances; The Choice Is Clear: Red, White & Blue . . . The Simple, Affordable, No-Braces Treatment; (product information), 6 pages; (year of pub. sufficiently earlier than effective US filing date and any foreign priority date) 2003.

Allesee Orthodontic Appliances; The Choice is Clear: Red, White & Blue . . . The Simple, Affordable, No-Braces Treatment; (Patient Information); retrieved from the internet (http://ormco.com/aoa/appliancesservices/RWB/patients.html); 2 pages on May 19, 2003.

Allesee Orthodontic Appliances; The Red, White & Blue Way to Improve Your Smile; (information for patients), 2 pages; (year of pub. sufficiently earlier than effective US filing date and any foreign priority date) 1992.

Allesee Orthodontic Appliances; You may be a candidate for this invisible no-braces treatment; product information for patients; 2 pages; (year of pub. sufficiently earlier than effective US filing date and any foreign priority date) 2002.

Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.

Altschuler et al.; Laser Electro-Optic System for Rapid Three-Dimensional (3D) Topographic Mapping of Surfaces; Optical Engineering; 20(6); pp. 953-961; Dec. 1981.

Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.

Altschuler; 3D Mapping of Maxillo-Facial Prosthesis; AADR Abstract #607; 2 pages total, (year of pub. sufficiently earlier than effective US filing date and any foreign priority date) 1980.

Andersson et al.; Clinical Results with Titanium Crowns Fabricated with Machine Duplication and Spark Erosion; Acta Odontologica Scandinavica; 47(5); pp. 279-286; Oct. 1989.

Andrews, The Six Keys to Optimal Occlusion Straight Wire, Chapter 3, L.A. Wells; pp. 13-24; (year of pub. sufficiently earlier than effective US filing date and any foreign priority date) 1989.

Bartels et al.; An Introduction to Splines for Use in Computer Graphics and Geometric Modeling; Morgan Kaufmann Publishers; pp. 422-425 Jan. 1, 1987.

Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972.

Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.

Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.

Baumrind; Integrated Three-Dimensional Craniofacial Mapping: Background, Principles, and Perspectives; Seminars in Orthodontics; 7(4); pp. 223-232; Dec. 2001.

beautyworlds.com; Virtual plastic surgery—beautysurge.com announces launch of cosmetic surgery digital imaging services; 5 pages;

(56) References Cited

OTHER PUBLICATIONS retrieved from the internet (http://www.beautyworlds.com/cosmossurgdigitalimagning.htm); Mar. 2004.

Begole et al.; A Computer System for the Analysis of Dental Casts; The Angle Orthodontist; 51(3); pp. 252-258; Jul. 1981.

Berland; The use of smile libraries for cosmetic dentistry; Dental Tribune: Asia Pacific Edition; pp. 16-18; Mar. 29, 2006.

Bernabe et al.; Are the lower incisors the best predictors for the unerupted canine and premolars sums? An analysis of Peruvian sample; The Angle Orthodontist; 75(2); pp. 202-207; Mar. 2005.

Bernard et al.; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.

Bhatia et al.; A Computer-Aided Design for Orthognathic Surgery; British Journal of Oral and Maxillofacial Surgery; 22(4); pp. 237-253; Aug. 1, 1984.

Biggerstaff et al.; Computerized Analysis of Occlusion in the Postcanine Dentition; American Journal of Orthodontics; 61(3); pp. 245-254; Mar. 1972.

Biggerstaff; Computerized Diagnostic Setups and Simulations; Angle Orthodontist; 40(I); pp. 28-36; Jan. 1970.

Biostar Operation & Training Manual. Great Lakes Orthodontics, Ltd. 199 Fire Tower Drive,Tonawanda, New York. 14150-5890, 20 pages; (year of pub. sufficiently earlier than effective US filing date and any foreign priority date) 1990.

Blu et al.; Linear interpolation revitalized; IEEE Transactions on Image Processing; 13(5); pp. 710-719; May 2004.

Bourke, Coordinate System Transformation; 1 page; retrived from the internet (http://astronomy.swin.edu.au/ pbourke/prolection/coords) on Nov. 5, 2004; Jun. 1996.

Boyd et al.; Three Dimensional Diagnosis and Orthodontic Treatment of Complex Malocclusions With the Invisalipn Appliance; Seminars in Orthodontics; 7(4); pp. 274-293; Dec. 2001.

Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.

Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.

Burstone et al.; Precision Adjustment of the Transpalatal Lingual Arch: Computer Arch Form Predetermination; American Journal of Orthodontics; 79(2);pp. 115-133; Feb. 1981.

Burstone; Dr. Charles J. Burstone on The Uses of the Computer in Orthodontic Practice (Part 1); Journal of Clinical Orthodontics; 13(7); pp. 442-453; (interview); Jul. 1979.

Burstone; Dr. Charles J. Burstone on The Uses of the Computer in Orthodontic Practice (Part 2); journal of Clinical Orthodontics; 13(8); pp. 539-551 (interview); Aug. 1979.

Cadent Inc.; OrthoCAD ABO user guide; 38 pages; Dec. 21, 2005.

Cadent Inc.; Reviewing and modifying an orthoCAD case; 4 pages; Feb. 14, 2005.

Cardinal Industrial Finishes; Powder Coatings; 6 pages; retrieved from the internet (http://www.cardinalpaint.com) on Aug. 25, 2000.

Carnaghan, An Alternative to Holograms for the Portrayal of Human Teeth; 4th Int'l. Conf. on Holographic Systems, Components and Applications; pp. 228-231; Sep. 15, 1993.

Chaconas et al,; The DigiGraph Work Station, Part 1, Basic Concepts; Journal of Clinical Orthodontics; 24(6); pp. 360-367; (Author Manuscript); Jun. 1990.

Chafetz et al.; Subsidence of the Femoral Prosthesis, A Stereophotogrammetric Evaluation; Clinical Orthopaedics and Related Research; No. 201; pp. 60-67; Dec. 1985.

Chiappone; Constructing the Gnathologic Setup and Positioner; Journal of Clinical Orthodontics; 14(2); pp. 121-133; Feb. 1980.

Chishti et al.; U.S. Appl. No. 60/050,342 entitled "Procedure for moving teeth using a seires of retainers," filed Jun. 20, 1997.

Collins English Dictionary; Teeth (definition); 9 pages; retrieved from the internet (https:www.collinsdictionary.com/us/dictionary/english/teeth) on May 13, 2019.

Cottingham; Gnathologic Clear Plastic Positioner; American Journal of Orthodontics; 55(1); pp. 23-31; Jan. 1969.

Crawford; CAD/CAM in the Dental Office: Does It Work?; Canadian Dental Journal; 57(2); pp. 121-123 Feb. 1991.

Crawford; Computers in Dentistry: Part 1: CAD/CAM: The Computer Moves Chairside, Part 2: F. Duret A Man With A Vision, Part 3: The Computer Gives New Vision—Literally, Part 4: Bytes 'N Bites The Computer Moves From The Front Desk To The Operatory; Canadian Dental Journal; 54(9); pp. 661-666 Sep. 1988.

Crooks; CAD/CAM Comes to USC; USC Dentistry; pp. 14-17; (year of pub. sufficiently earlier than effective US filing date and any foreign priority date) Spring 1990.

CSI Computerized Scanning and Imaging Facility; What is a maximum/minimum intensity projection (MIP/MinIP); 1 page; retrived from the internet (http://csi.whoi.edu/content/what-maximumminimum-intensity-projection-mipminip); Jan. 4, 2010.

Cureton; Correcting Malaligned Mandibular Incisors with Removable Retainers; Journal of Clinical Orthodontics; 30(7); pp. 390-395; Jul. 1996.

Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.

Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.

DCS Dental AG; The CAD/CAM 'DCS Titan System' for Production of Crowns/Bridges; DSC Production; pp. 1-7; Jan. 1992.

DeFranco et al.; Three-Dimensional Large Displacement Analysis of Orthodontic Appliances; Journal of Biomechanics; 9(12); pp. 793-801; Jan. 1976.

Dental Institute University of Zurich Switzerland; Program for International Symposium on Computer Restorations: State of the Art of the CEREC-Method; 2 pages; May 1991.

Dental Monitoring; Basics: Howto put the cheek retractor?; 1 page (Screenshot); retrieved from the interenet (https://www.youtube.com/watch?v=6K1HXw4Kq3c); May 27, 2016.

Dental Monitoring; Dental monitoring tutorial; 1 page (Screenshot); retrieved from the internet (https:www.youtube.com/watch?v=Dbe3udOf9_c); Mar. 18, 2015.

Dentrac Corporation; Dentrac document; pp. 4-13; (year of pub. sufficiently earlier than effective US filing date and any foreign priority date) 1992.

Dentrix; Dentrix G3, new features; 2 pages; retrieved from the internet (http://www.dentrix.com/g3/new_features/index.asp); on Jun. 6, 2008.

Dent-x; Dentsim . . . Dent-x's virtual reality 3-D training simulator . . . A revolution in dental education; 6 pages; retrieved from the internet (http://www.dent-x.com/DentSim.htm); on Sep. 24, 1998.

Di Giacomo et al.; Clinical application of sterolithographic surgical guides for implant placement: Preliminary results; Journal Periodontolgy; 76(4); pp. 503-507; Apr. 2005.

Di Muzio et al.; Minimum intensity projection (MinIP); 6 pages; retrieved from the internet (https://radiopaedia.org/articles/minimum-intensity-projection-minip) on Sep. 6, 2018.

DICOM to surgical guides; (Screenshot)l page; retrieved from the internet at YouTube (https://youtu.be/47KtOmCEFQk); Published Apr. 4, 2016.

dictionary.com; Plural (definition); 6 pages; retrieved from the internet ( https://www.dictionary.eom/browse/plural#) on May 13, 2019.

dictionary.com; Quadrant (definition); 6 pages; retrieved from the internet ( https://www.dictionary.com/browse/quadrant?s=t) on May 13, 2019.

Doruk et al.; The role of the headgear timer in extraoral cooperation; European Journal of Orthodontics; 26; pp. 289-291; Jun. 1, 2004.

Doyle; Digital Dentistry; Computer Graphics World; pp. 50-52 and p. 54; Oct. 2000.

(56) References Cited

OTHER PUBLICATIONS

Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.
Duret et al.; CAD/CAM Imaging in Dentistry; Current Opinion in Dentistry; 1(2); pp. 150-154; Apr. 1991.
Duret et al; CAD-CAM in Dentistry; Journal of the American Dental Association; 117(6); pp. 715-720; Nov. 1988.
Duret; The Dental CAD/CAM, General Description of the Project; Hennson International Product Brochure, 18 pages; Jan. 1986.
Duret; Vers Une Prosthese Informatisee; Tonus; 75(15); pp. 55-57; (English translation attached); 23 pages; Nov. 15, 1985.
Ecligner Selfie; Change your smile; 1 page (screenshot); retrieved from the internet (https:play.google.com/store/apps/details?id=parklict.ecligner); on Feb. 13, 2018.
Economides; The Microcomputer in the Orthodontic Office; Journal of Clinical Orthodontics; 13(11); pp. 767-772; Nov. 1979.
Elsasser; Some Observations on the History and Uses of the Kesling Positioner; American Journal of Orthodontics; 36(5); pp. 368-374; May 1, 1950.
English translation of Japanese Laid-Open Publication No. 63-11148 to inventor T. Ozukuri (Laid-Open on Jan. 18, 1998) pp. 1-7.
Faber et al.; Computerized Interactive Orthodontic Treatment Planning; American Journal of Orthodontics; 73(1); pp. 36-46; Jan. 1978.
Felton et al.; A Computerized Analysis of the Shape and Stability of Mandibular Arch Form; American Journal of Orthodontics and Dentofacial Orthopedics; 92(6); pp. 478-483; Dec. 1987.
Friede et al.; Accuracy of Cephalometric Prediction in Orthognathic Surgery; Journal of Oral and Maxillofacial Surgery; 45(9); pp. 754-760; Sep. 1987.
Friedrich et al; Measuring system for in vivo recording of force systems in orthodontic treatment-concept and analysis of accuracy; J. Biomech.; 32(1); pp. 81-85; (Abstract Only) Jan. 1999.
Futterling et al.; Automated Finite Element Modeling of a Human Mandible with Dental Implants; JS WSCG '98-Conference Program; 8 pages; retrieved from the Internet (https://dspace5.zcu.ez/bitstream/11025/15851/1/Strasser_98.pdf); on Aug. 21, 2018.
Gansky; Dental data mining: potential pitfalls and practical issues; Advances in Dental Research; 17(1); pp. 109-114; Dec. 2003.
Gao et al.; 3-D element Generation for Multi-Connected Complex Dental and Mandibular Structure; IEEE Proceedings International Workshop in Medical Imaging and Augmented Reality; pp. 267-271; Jun. 12, 2001.
Geomagic; Dental reconstruction; 1 page; retrieved from the internet (http://geomagic.com/en/solutions/industry/detal_desc.php) on Jun. 6, 2008.
Gim-Alldent Deutschland, "Das DUX System: Die Technik," 3 pages; (English Translation Included); (year of pub. sufficiently earlier than effective US filing date and any foreign priority date); 2002.
Gottleib et al.; JCO Interviews Dr. James A. McNamura, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982&Month=06&ArticleNum+); 21 pages; Jun. 1982.
gpsdentaire.com; Get a realistic smile simulation in 4 steps with GPS; a smile management software; 10 pages; retrieved from the internet (http://www.gpsdentaire.com/en/preview/) on Jun. 6, 2008.
Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.
Grest, Daniel; Marker-Free Human Motion Capture in Dynamic Cluttered Environments from a Single View-Point, PhD Thesis; 171 pages; Dec. 2007.
Guess et al.; Computer Treatment Estimates In Orthodontics and Orthognathic Surgery; Journal of Clinical Orthodontics; 23(4); pp. 262-268; 11 pages; (Author Manuscript); Apr. 1989.

Heaven et al.; Computer-Based Image Analysis of Artificial Root Surface Caries; Abstracts of Papers #2094; Journal of Dental Research; 70:528; (Abstract Only); Apr. 17-21, 1991.
Highbeam Research; Simulating stress put on jaw. (ANSYS Inc.'s finite element analysis software); 2 pages; retrieved from the Internet (http://static.highbeam.eom/t/toolingampproduction/november011996/simulatingstressputonfa . . . ); on Nov. 5, 2004.
Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Included); Feb. 1987.
Hoffmann et al.; Role of Cephalometry for Planning of Jaw Orthopedics and Jaw Surgery Procedures; Informatbnen, pp. 375-396; (English Abstract Included); Mar. 1991.
Hojjatie et al.; Three-Dimensional Finite Element Analysis of Glass-Ceramic Dental Crowns; Journal of Biomechanics; 23(11); pp. 1157-1166; Jan. 1990.
Huckins; CAD-CAM Generated Mandibular Model Prototype from MRI Data; AAOMS, p. 96; (Abstract Only); (year of pub. sufficiently earlier than effective US filing date and any foreign priority date) 1999.
Invisalign; You were made to move. There's never been a better time to straighten your teeth with the most advanced clear aligner in the world; Product webpage; 2 pages; retrieved from the internet (www.invisalign.com/) on Dec. 28, 2017.
JCO Interviews; Craig Andreiko , DDS, MS on the Elan and Orthos Systems; Interview by Dr. Larry W. White; Journal of Clinical Orthodontics; 28(8); pp. 459-468; 14 pages; (Author Manuscript); Aug. 1994.
JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.
Jerrold; The Problem, Electronic Data Transmission and the Law; American Journal of Orthodontics and Dentofacial Orthopedics; 113(4); pp. 478-479; 5 pages; (Author Manuscript); Apr. 1998.
Jones et al.; An Assessment of the Fit of a Parabolic Curve to Pre- and Post-Treatment Dental Arches; British Journal of Orthodontics; 16(2); pp. 85-93; May 1989.
Kamada et.al.; Case Reports On Tooth Positioners Using LTV Vinyl Silicone Rubber; J. Nihon University School of Dentistry; 26(1); pp. 11-29; (year of pub. sufficiently earlier than effective US filing date and any foreign priority date) 1984.
Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.
Kanazawa et al.; Three-Dimensional Measurements of the Occlusal Surfaces of Upper Molars in a Dutch Population; Journal of Dental Research; 63(11); pp. 1298-1301; Nov. 1984.
Karaman et al.; A practical method of fabricating a lingual retainer; Am. Journal of Orthodontic and Dentofacial Orthopedics; 124(3); pp. 327-330; Sep. 2003.
Kesling et al.; The Philosophy of the Tooth Positioning Appliance; American Journal of Orthodontics and Oral surgery; 31(6); pp. 297-304; Jun. 1945.
Kesling; Coordinating the Predetermined Pattern and Tooth Positioner with Conventional Treatment; American Journal of Orthodontics and Oral Surgery; 32(5); pp. 285-293; May 1946.
Kleeman et al.; The Speed Positioner; J. Clin. Orthod.; 30(12); pp. 673-680; Dec. 1996.
Kochanek; Interpolating Splines with Local Tension, Continuity and Bias Control; Computer Graphics; 18(3); pp. 33-41; Jan. 1, 1984.
Kunii et al.; Articulation Simulation for an Intelligent Dental Care System; Displays; 15(3); pp. 181-188; Jul. 1994.
Kuroda et al.; Three-Dimensional Dental Cast Analyzing System Using Laser Scanning; American Journal of Orthodontics and Dentofacial Orthopedics; 110(4); pp. 365-369; Oct. 1996.
Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.

(56) References Cited

OTHER PUBLICATIONS

Lawrence; Salivary markers of systemic disease: noninvasive diagnosis of disease and monitoring of general health; Journal of the Canadian Dental Association Clinical Practice; 68(3); pp. 170-174; Mar. 2002.
Leinfelder et al.; A New Method for Generating Ceramic Restorations: a CAD-CAM System; Journal of the American Dental Association; 118(6); pp. 703-707; Jun. 1989.
Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filing date and any foreign priority date) 1983.
Mantzikos et al.; Case report: Forced eruption and implant site development; The Angle Orthodontist; 68(2); pp. 179-186; Apr. 1998.
Martinelli et al.; Prediction of lower permanent canine and premolars width by correlation methods; The Angle Orthodontist; 75(5); pp. 805-808; Sep. 2005.
McCann; Inside the ADA; J. Amer. Dent. Assoc, 118:286-294; Mar. 1989.
McNamara et al.; Invisible Retainers; J. Clin Orthod.; pp. 570-578; 11 pages; (Author Manuscript); Aug. 1985.
McNamara et al.; Orthodontic and Orthopedic Treatment in the Mixed Dentition; Needham Press; pp. 347-353; Jan. 1993.
Methot; Get the picture with a gps for smile design in 3 steps; Spectrum; 5(4); pp. 100-105; (year of pub. sufficiently earlier than effective US filing date and any foreign priority date) 2006.
Moermann et al, Computer Machined Adhesive Porcelain Inlays: Margin Adaptation after Fatigue Stress; IADR Abstract 339; J. Dent. Res.; 66(a):763; (Abstract Only); (year of pub. sufficiently earlier than effective US filing date and any foreign priority date) 1987.
Moles; Correcting Mild Malalignments—As Easy As One, Two, Three; AOA/Pro Corner; 11(2); 2 pages; (year of pub. sufficiently earlier than effective US filing date and any foreign priority date) 2002.
Mormann et al.; Marginale Adaptation von adhasuven Porzellaninlays in vitro; Separatdruck aus:Schweiz. Mschr. Zahnmed.; 95; pp. 1118-1129; 8 pages; (Machine Translated English Abstract); (year of pub. sufficiently earlier than effective US filing date and any foreign priority date); 1985.
Nahoum; The Vacuum Formed Dental Contour Appliance; N. Y. State Dent. J.; 30(9); pp. 385-390; Nov. 1964.
Nash; CEREC CAD/CAM Inlays: Aesthetics and Durability in a Single Appointment; Dentistry Today; 9(8); pp. 20, 22-23 and 54; Oct. 1990.
Newcombe; DTAM: Dense tracking and mapping in real-time; 8 pages; retrieved from the internet (http://www.doc.ic.ac.uk/?ajd/Publications/newcombe_etal_iccv2011.pdf; on Dec. 2011.
Nishanian et al.; Oral fluids as an alternative to serum for measurement of markers of immune activation; Clinical and Diagnostic Laboratory Immunology; 5(4); pp. 507-512; Jul. 1998.
Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.
Nourallah et al.; New regression equations for prediciting the size of unerupted canines and premolars in a contemporary population; The Angle Orthodontist; 72(3); pp. 216-221; Jun. 2002.
Ogawa et al.; Mapping, profiling and clustering of pressure pain threshold (PPT) in edentulous oral muscosa; Journal of Dentistry; 32(3); pp. 219-228; Mar. 2004.
Ogimoto et al.; Pressure-pain threshold determination in the oral mucosa; Journal of Oral Rehabilitation; 29(7); pp. 620-626; Jul. 2002.
ormco.com; Increasing clinical performance with 3D interactive treatment planning and patient-specific appliances; 8 pages; retrieved from the internet (http://www.konsident.com/wp-content/files_mf/1295385693http___ormco.com_index_cmsfilesystemaction_fileOrmcoPDF_whitepapers.pdf) on Feb. 27, 2019.
OrthoCAD downloads; retrieved Jun. 27, 2012 from the internet (www.orthocad.com/download/downloads.asp); 2 pages; Feb. 14, 2005.
Page et al.; Validity and accuracy of a risk calculator in predicting periodontal disease; Journal of the American Dental Association; 133(5); pp. 569-576; May 2002.
Paredes et al.; A new, accurate and fast digital method to predict unerupted tooth size; The Angle Orthodontist; 76(1); pp. 14-19; Jan. 2006.
Patterson Dental; Cosmetic imaging; 2 pages retrieved from the internet (http://patterson.eaglesoft.net/cnt_di_cosimg.html) on Jun. 6, 2008.
Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4; pp. 2415-2418; Sep. 4, 1998.
Pinkham; Foolish Concept Propels Technology; Dentist, 3 pages , Jan./Feb. 1989.
Pinkham; Inventor's CAD/CAM May Transform Dentistry; Dentist; pp. 1 and 35, Sep. 1990.
Ponitz; Invisible retainers; Am. J. Orthod.; 59(3); pp. 266-272; Mar. 1971.
Procera Research Projects; Procera Research Projects 1993 Abstract Collection; 23 pages; (year of pub. sufficiently earlier than effective US filing date and any foreign priority date) 1993.
Proffit et al.; The first stage of comprehensive treatment alignment and leveling; Contemporary Orthodontics, 3rd Ed.; Chapter 16; Mosby Inc.; pp. 534-537; (year of pub. sufficiently earlier than effective US filing date and any foreign priority date) 2000.
Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.
Raintree Essix & ARS Materials, Inc., Raintree Essix, Technical Magazine Table of contents and Essix Appliances, 7 pages; retrieved from the internet (http://www.essix.com/magazine/defaulthtml) on Aug. 13, 1997.
Redmond et al.; Clinical Implications of Digital Orthodontics; American Journal of Orthodontics and Dentofacial Orthopedics; 117(2); pp. 240-242; Feb. 2000.
Rekow et al.; CAD/CAM for Dental Restorations—Some of the Curious Challenges; IEEE Transactions on Biomedical Engineering; 38(4); pp. 314-318; Apr. 1991.
Rekow et al.; Comparison of Three Data Acquisition Techniques for 3-D Tooth Surface Mapping; Annual International Conference of the IEEE Engineering in Medicine and Biology Society; 13(1); pp. 344-345 (year of pub. sufficiently earlier than effective US filing date and any foreign priority date) 1991.
Rekow; A Review of the Developments in Dental CAD/CAM Systems; Current Opinion in Dentistry; 2; pp. 25-33; Jun. 1992.
Rekow; CAD/CAM in Dentistry: A Historical Perspective and View of the Future; Journal Canadian Dental Association; 58(4); pp. 283, 287-288; Apr. 1992.
Rekow; Computer-Aided Design and Manufacturing in Dentistry: A Review of the State of the Art; Journal of Prosthetic Dentistry; 58(4); pp. 512-516; Dec. 1987.
Rekow; Dental CAD-CAM Systems: What is the State of the Art?; The Journal of the American Dental Association; 122(12); pp. 43-48; Dec. 1991.
Rekow; Feasibility of an Automated System for Production of Dental Restorations, Ph.D. Thesis; Univ. of Minnesota, 250 pages, Nov. 1988.
Richmond et al.; The Development of the PAR Index (Peer Assessment Rating): Reliability and Validity.; The European Journal of Orthodontics; 14(2); pp. 125-139; Apr. 1992.
Richmond et al.; The Development of a 3D Cast Analysis System; British Journal of Orthodontics; 13(1); pp. 53-54; Jan. 1986.
Richmond; Recording The Dental Cast In Three Dimensions; American Journal of Orthodontics and Dentofacial Orthopedics; 92(3); pp. 199-206; Sep. 1987.

(56) References Cited

OTHER PUBLICATIONS

Rose et al.; The role of orthodontics in implant dentistry; British Dental Journal; 201(12); pp. 753-764; Dec. 23, 2006.
Rubin et al.; Stress analysis of the human tooth using a three-dimensional finite element model; Journal of Dental Research; 62(2); pp. 82-86; Feb. 1983.
Rudge; Dental Arch Analysis: Arch Form, A Review of the Literature; The European Journal of Orthodontics; 3(4); pp. 279-284; Jan. 1981.
Sahm et al.; "Micro-Electronic Monitoring Of Functional Appliance Wear"; Eur J Orthod.; 12(3); pp. 297-301; Aug. 1990.
Sahm; Presentation of a wear timer for the clarification of scientific questions in orthodontic orthopedics; Fortschritte der Kieferorthopadie; 51 (4); pp. 243-247; (Translation Included) Jul. 1990.
Sakuda et al.; Integrated Information-Processing System In Clinical Orthodontics: An Approach with Use of a Computer Network System; American Journal of Orthodontics and Dentofacial Orthopedics; 101(3); pp. 210-220; 20 pages; (Author Manuscript) Mar. 1992.
Sarment et al.; Accuracy of implant placement with a sterolithographic surgical guide; journal of Oral and Maxillofacial Implants; 118(4); pp. 571-577; Jul. 2003.
Schellhas et al.; Three-Dimensional Computed Tomography in Maxillofacial Surgical Planning; Archives of Otolaryngology—Head and Neck Surgery; 114(4); pp. 438-442; Apr. 1988.
Schroeder et al; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.
Shilliday; Minimizing finishing problems with the mini-positioner; American Journal of Orthodontics; 59(6); pp. 596-599; Jun. 1971.
Siemens; CEREC—Computer-Reconstruction, High Tech in der Zahnmedizin; 15 pagesl; (Includes Machine Translation); (year of pub. sufficiently earlier than effective US filing date and any foreign priority date); 2004.
Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.
Sirona Dental Systems GmbH, CEREC 3D, Manuel utiiisateur, Version 2.0X (in French); 114 pages; (English translation of table of contents included); (year of pub. sufficiently earlier than effective US filing date and any foreign priority date); 2003.
Smalley; Implants for tooth movement: Determining implant location and orientation: Journal of Esthetic and Restorative Dentistry; 7(2); pp. 62-72; Mar. 1995.
Smart Technology; Smile library II; 1 page; retrieved from the internet (http://smart-technology.net/) on Jun. 6, 2008.
Smile-Vision_The smile-vision cosmetic imaging system; 2 pages; retrieved from the internet (http://www.smile-vision.net/cos_imaging.php) on Jun. 6, 2008.
Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.
Sturman; Interactive Keyframe Animation of 3-D Articulated Models; Proceedings Graphics Interface '84; vol. 86; pp. 35-40; May-Jun. 1984.
Svec et al.; Molded rigid monolithic porous polymers: an inexpensive, efficient, and versatile alternative to beads for design of materials for numerous applications; Industrial and Engineering Chemistry Research; 38(1); pp. 34-48; Jan. 4, 1999.
Szeliski; Introduction to computer vision: Structure from motion; 64 pages; retrieved from the internet (http://robots.stanford.edu/cs223b05/notes/CS%20223-B%20L10%structurefrommotion1b.ppt, on Feb. 3, 2005.
The American Heritage, Stedman's Medical Dictionary; Gingiva; 3 pages; retrieved from the interent (http://reference.com/search/search?q=gingiva) on Nov. 5, 2004.

Thera Mon; "Microsensor"; 2 pages; retrieved from the internet (www.english.thera-mon.com/the-product/transponder/index.html); on Sep. 19, 2016.
Thorlabs; Pellin broca prisms; 1 page; retrieved from the internet (www.thorlabs.com); Nov. 30, 2012.
Tiziani et al.; Confocal principle for macro and microscopic surface and defect analysis; Optical Engineering; 39(1); pp. 32-39; Jan. 1, 2000.
Truax; Truax Clasp-Less(TM) Appliance System; The Functional Orthodontist; 9(5); pp. 22-24, 26-28; Sep.-Oct. 1992.
Tru-Tatn Orthodontic & Dental Supplies, Product Brochure, Rochester, Minnesota 55902, 16 pages; (year of pub. sufficiently earlier than effective US filing date and any foreign priority date) 1996.
U.S. Department of Commerce, National Technical Information Service, Holodontography: An Introduction to Dental Laser Holography; School of Aerospace Medicine Brooks AFB Tex; Mar. 1973, 40 pages; Mar. 1973.
U.S. Department of Commerce, National Technical Information Service; Automated Crown Replication Using Solid Photography SM; Solid Photography Inc., Melville NV,; 20 pages; Oct. 1977.
U.S. Food and Drug Administration; Color additives; 3 pages; retrieved from the internet (https://websrchive.org/web/20070502213911/http://www.cfsan.fda.gov/~dms/col-toc.html); last known as May 2, 2007.
Vadapalli; Minimum intensity projection (MinIP) is a data visualization; 7 pages; retrieved from the internet (https://prezi.com/tdmttnmv2knw/minimum-intensity-projection-minip-is-a-data-visualization/) on Sep. 6, 2018.
Van Der Linden et al.; Three-Dimensional Analysis of Dental Casts by Means of the Optocom; Journal of Dental Research; 51(4); p. 1100; Jul.-Aug. 1972.
Van Der Linden; A New Method to Determine Tooth Positions and Dental Arch Dimensions; Journal of Dental Research; 51(4); p. 1104; Jul.-Aug. 1972.
Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.
Varady et al.; Reverse Engineering Of Geometric Models$^{ADDAC;AG0}$ An Introduction; Computer-Aided Design; 29(4); pp. 255-268; 20 pages; (Author Manuscript); Apr. 1997.
Verstreken et al.; An Image-Guided Planning System for Endosseous Oral Implants; IEEE Transactions on Medical Imaging; 17(5); pp. 842-852; Oct. 1998.
Vevin et al.; Pose estimation of teeth through crown-shape matching; In Medical Imaging: Image Processing of International Society of Optics and Photonics; vol. 4684; pp. 955-965; May 9, 2002.
Virtual Orthodontics; Our innovative software; 2 pages; (http://www.virtualorthodontics.com/innovativesoftware.html); retrieved from the internet (https://web.archive.org/web/20070518085145/http://www.virtualorthodontics.com/innovativesoftware.html); (year of pub. sufficiently earlier than effective US filing date and any foreign priority date) 2005.
Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.
Warunek et.al.; Clinical Use of Silicone Elastomer Applicances; JCO; 23(10); pp. 694-700; Oct. 1989.
Watson et al.; Pressures recorded at te denture base-mucosal surface interface in complete denture wearers; Journal of Oral Rehabilitation 14(6); pp. 575-589; Nov. 1987.
Wells; Application of the Positioner Appliance in Orthodontic Treatment; American Journal of Orthodontics; 58(4); pp. 351-366; Oct. 1970.
Wiedmann; According to the laws of harmony to find the right tooth shape with assistance of the computer; Digital Dental News; 2nd vol.; pp. 0005-0008; (English Version Included); Apr. 2008.
Wikipedia; Palatal expansion; 3 pages; retrieved from the internet (https://en.wikipedia.org/wiki/Palatal_expansion) on Mar. 5, 2018.
Williams; Dentistry and CAD/CAM: Another French Revolution; J. Dent. Practice Admin.; 4(1); pp. 2-5 Jan./Mar. 1987.

(56) References Cited

OTHER PUBLICATIONS

Williams; The Switzerland and Minnesota Developments in CAD/CAM; Journal of Dental Practice Administration; 4(2); pp. 50-55; Apr./Jun. 1987.
Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery; p. 5; Presented on Sep. 13, 1990.
Witt et al.; The wear-timing measuring device in orthodontics-cui bono? Reflections on the state-of-the-art in wear-timing measurement and compliance research in orthodontics; Fortschr Kieferorthop.; 52(3); pp. 117-125; (Translation Included) Jun. 1991.
Wolf; Three-dimensional structure determination of semi-transparent objects from holographic data; Optics Communications; 1(4); pp. 153-156; Sep. 1969.
Wong et al.; Computer-aided design/computer-aided manufacturing surgical guidance for placement of dental implants: Case report; Implant Dentistry; 16(2); pp. 123-130; Sep. 2007.
Wong et al.; The uses of orthodontic study models in diagnosis and treatment planning; Hong Kong Dental Journal; 3(2); pp. 107-115; Dec. 2006.
WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.
Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.
Yaltara Software; Visual planner; 1 page; retrieved from the internet (http://yaltara.com/vp/) on Jun. 6, 2008.
Yamada et al.; Simulation of fan-beam type optical computed-tomography imaging of strongly scattering and weakly absorbing media; Applied Optics; 32(25); pp. 4808-4814; Sep. 1, 1993.
Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.
Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.
Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998.
Yoshii; Research on a New Orthodontic Appliance: The Dynamic Positioner (D.P.); III. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.
Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.
Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.
Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.
Zhang et al.; Visual speech features extraction for improved speech recognition; 2002 IEEE International conference on Acoustics, Speech and Signal Processing; vol. 2; 4 pages; May 13-17, 2002.
Shanjani et al., U.S. Appl. No. 16/206,894 entitled "Sensors for monitoring oral appliances," filed Nov. 28, 2019.
Shanjani et al., U.S. Appl. No. 16/231,906 entitled "Augmented reality enhancements for dental practitioners." Dec. 24, 2018.
Kopleman et al., U.S. Appl. No. 16/220,381 entitled "Closed loop adaptive orthodontic treatment methods and apparatuses," Dec. 14, 2018.
Sabina et al., U.S. Appl. No. 16/258,516 entitled "Diagnostic intraoral scanning" filed Jan. 25, 2019.
Sabina et al., U.S. Appl. No. 16/258,523 entitled "Diagnostic intraoral tracking" filed Jan. 25, 2019.
Sabina et al., U.S. Appl. No. 16/258,527 entitled "Diagnostic intraoral methods and apparatuses" filed Jan. 25, 2019.
Culp; U.S. Appl. No. 16/236,220 entitled "Laser cutting," filed Dec. 28, 2018.
Arnone et al.; U.S. Appl. No. 16/235,449 entitled "Method and system for providing indexing and cataloguing of orthodontic related treatment profiles and options," filed Dec. 28, 2018.
Mason et al.; U.S. Appl. No. 16/374,648 entitled "Dental condition evaluation and treatment," filed Apr. 3, 2019.
Brandt et al.; U.S. Appl. No. 16/235,490 entitled "Dental wire attachment," filed Dec. 28, 2018.
Chen et al.; U.S. Appl. No. 16/223,019 entitled "Release agent receptacle," filed Dec. 17, 2018.

* cited by examiner

INDIVIDUALIZED ORTHODONTIC TREATMENT INDEX

RELATED APPLICATIONS

The present application is a continuation of U.S. patent application Ser. No. 12/771,472, filed Apr. 30, 2010, the disclosure of which is incorporated in its entirety herein by reference.

BACKGROUND

The present disclosure is related generally to the field of orthodontics. More particularly, the present disclosure is related to using an individualized orthodontic treatment index.

Some objectives in the field of orthodontics are to realign a patient's teeth to positions where the teeth function well and align the teeth to provide a pleasing aesthetic appearance. One goal of an orthodontic treatment professional is to take the patient's dentition from a starting arrangement to a final arrangement.

Further, when using fixed brackets and wires (i.e., braces) may be applied to a patient's teeth to gradually reposition them from an initial arrangement to a final arrangement. The diagnosis and treatment planning process of orthodontic cases may be imprecise as the final dentition of a patient may be based on the knowledge and expertise of the treatment professional in assembling various parameters in an assessment of each patient's condition and in a determination of a final position for each tooth. Different treatment professionals may vary in their definitions of individual orthodontic parameters and their definition of how a case should ideally be treated may also vary.

To overcome some of these subjective issues, various indices have been used to more objectively define a patient's dentition, including initial dentition, progress dentition, and final outcome dentition. For example, the PAR (Peer Assessment Rating) index identifies how far a dentition is from a good occlusion. A score is assigned to various occlusal traits which make up a malocclusion. The individual scores are summed to obtain an overall total, representing the degree a case deviates from ideal functional alignment and occlusion. The PAR score is then calibrated to a known standard set of orthodontic conditions so this individual is able to rate new cases similarly. The PAR score may be weighted or unweighted, depending on the relative importance of certain components of the occlusion.

In PAR, a score of zero would indicate ideal alignment and positioning of all orthodontic dental components, as defined by generally accepted occlusal and aesthetic relationships the orthodontic community has adopted. Higher scores would indicate increased levels of irregularity. The PAR score can be recorded on pre-, mid- and/or post-treatment dental casts. The difference between any two of these scores represents the degree of improvement as a result of orthodontic intervention during the represented portion of treatment. The score may be represented as an absolute point improvement or as a percentage improvement with respect to an earlier treatment point used for the comparison.

In addition to the PAR index, other indices may be used such as Index of Complexity Outcome and Need (ICON), Index of Orthodontic Treatment Need (IOTN) and American Board of Orthodontics (ABO) indices. These indices also rely on individual dental measurements in order to derive an assessment of deviation from an ideal. One drawback to using such indices is that the individual dental measurements may be based on landmarks that are identified on the patient's dentition by a treatment professional. After identifying landmarks at an earlier stage of treatment, the treatment professional may not be able to accurately identify the same landmarks at a later stage of treatment because the patient's dentition may have changed during the course of treatment.

DETAILED DESCRIPTION

Figure 1A:
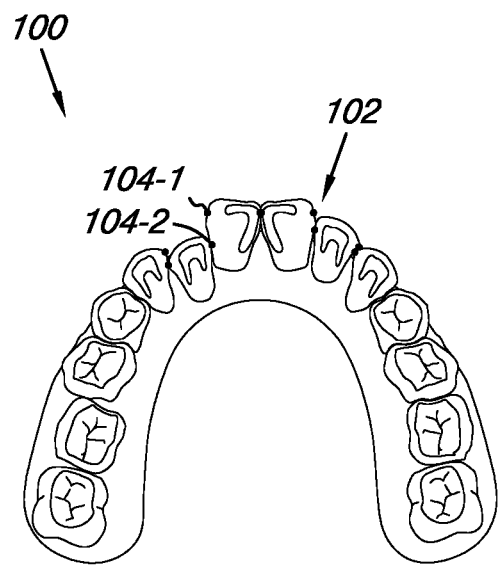
FIG. 1A illustrates an initial virtual dental model having dental references assigned thereto according to a prior art method.

Embodiments of the present disclosure include computing device related, system, and method embodiments for using an individualized orthodontic treatment index. For example, one or more embodiments include, a computing device implemented method that includes receiving an initial virtual dental model from a first scan of a patient's dentition, modifying the initial virtual dental model to create a target virtual dental model according to a treatment goal, and assigning a number of dental references to the target virtual dental model.

The first scan of the patient's dentition can be a scan performed prior to treatment initiation or before the completion of treatment. Assigning dental references to the target virtual dental model can be beneficial as compared to assigning target dental references to the initial virtual dental model (e.g., assigning dental references to the initial model in positions where the treatment professional believes they should be) because the correct location of certain landmarks such as contact points and cusp tips (which may have some degree of uncertainty in identifying when using the initial state) may be more accurate when using the context of the desired final outcome to assist in the identification process.

Some embodiments can include receiving a treatment outcome virtual dental model from a second scan of the patient's dentition and mapping the number of dental references from the target virtual dental model to the treatment outcome virtual dental model. The second scan of the patient's dentition can be a scan performed after treatment has been completed or after some portion of treatment has been completed. Mapping landmarks established on the treatment target virtual dental model to the treatment outcome virtual dental model can provide for a more accurate assessment and comparison between the actual treatment outcome achieved and the target treatment outcome for the patient because the same reference points are being used to derive measurements in both the initial and outcome models. Mapping can help reduce errors associated with misidentification of landmarks between different models.

Embodiments can include calculating an initial deviation from ideal using a target-normalized setup as an "ideal." As opposed to some previous approaches, the individualized treatment index score can be relevant to all types of cases and not just permanent non-worn, ideally shaped patient dentition. For example, an occlusion score can be established for restored, primary, and/or worn dentition without these conditions negatively contributing to the score. By having broader applicability, the individualized treatment index score can establish baselines of quality for a wider array of treatment applications.

Embodiments can include calculating an individualized treatment index score for the actual treatment outcome through a virtual dental model of the outcome according to one or more differences between the target virtual dental model and the treatment outcome virtual dental model based on the number of mapped dental references. This can improve the accuracy of measurements by reducing the error introduced from landmark identification on models representing multiple points in treatment when such models are evaluated individually.

Treatment professionals typically establish their target as the ideal treatment outcome based upon one or more of these scoring systems and discontinue treatment when they are as close as they can possibly get to the ideal treatment outcome. However, with the use of 3-D computer graphics software services and programs, the treatment professional can establish a custom treatment target specific to each individual patient, and this target may be a limited treatment target and not ideal in every component. In part, this may be due to unwillingness by the patient to undergo certain aspects of treatment in order to achieve an ideal outcome (e.g., jaw surgery, headgear, elective restorative dental care, etc.).

Thus, if the treatment professional is able to achieve 100% of the intended limited target, the treatment may still be deemed a success, even though the target might only represent a 75% improvement relative to an ideal target. Without characterizing the degree of improvement relative to the intended target, a treatment might be mistakenly categorized as being unsuccessful when it was highly successful in the eyes of both the treatment professional and the patient. According to the present disclosure, a context of the intended individual treatment goal can determine the degree of treatment success achieved, rather than an absolute index.

Some clinical measurements are benchmarked against standards using relationships between specific dental landmarks. A degree of error can be introduced into scoring a dental model and/or calculating an index score based on the selection of a specific reference (e.g., landmark) and/or based on the repeatability of the selection between different models (e.g., representing different points in treatment). The accuracy to which the landmark is selected and/or repeated by the user can determine whether or not the measurement represents the correct relationship found in the model.

A user may have difficulty in identifying a specific dental landmark due to the shape of the patient's anatomy. For example, proper identification of a cusp tip may be hindered by the tooth having been worn down. Furthermore, the "same" reference point may be inadvertently selected at different locations on different dental models that represent different treatment points for the patient.

Virtual dental models from a scan of a patient's dentition can be provided with computer-aided tooth treatment systems. An initial digital data set (IDDS) representing an initial tooth arrangement may be obtained. The IDDS may be obtained in a variety of ways. For example, the patient's teeth may be imaged to obtain digital data using direct or indirect structured light, X-rays, three-dimensional X-rays, computer-aided tomographic images or data sets, magnetic resonance images, photographic reconstruction, and/or other imaging techniques.

A cast (e.g., a plaster cast and/or mold) of the patient's teeth may be scanned using an x-ray, laser scanner, destructive scanner, structured light, or other range acquisition system to produce the IDDS. The data set produced by the range acquisition system may be converted to other formats to be compatible with the software which is used for manipulating images within the data set, as described herein.

The data set can be used to create a series of orthodontic aligners used to move teeth though successive arrangements from molds of the patient's teeth or digital models of the patient's teeth. One example of such a system is described in more detail in U.S. Pat. No. 5,975,893 to Chisti et al., which is assigned to Align Technology, Inc.

Although the overarching term "orthodontics" is used herein, the present disclosure may relate to treatments of an orthognathic nature. For example, in cases including treatment of a patient's underlying skeletal structure, teeth may be rearranged by surgically repositioning underlying bones that hold the teeth in order to achieve a desired final bite arrangement. In both orthodontic and orthognathic treatment approaches, alignment of the teeth may be evaluated pre-, mid-, and/or post-treatment.

Referring now to FIG. 1A, there is illustrated an initial virtual dental model having dental references assigned thereto according to a prior art method. The prior art method includes identifying the dental references 102 (e.g., contact points 104-1 and 104-2 between various teeth as illustrated in FIG. 1A). The treatment professional can use his/her best judgment to identify and assign the dental references 102 to the initial virtual dental model 100.

After the dental references 102 have been assigned to the initial virtual dental model 100, a score can be calculated according to a prior art method such as PAR, ICON, IOTN, and ABO, as described herein. For example, a score can be calculated based on a measurement of the distance between contact points 104-1 and 104-2, where an "ideal" case would have substantially zero distance between contact points 104-1 and 104-2 for various teeth. Scores for cases varying from the ideal can have a higher value.

For the various prior art methods, the ideal case is a pre-defined orthodontic norm with assumptions about the phase, shape, and condition of the teeth. Again, scoring based on such an ideal case assumes that the ideal can actually be achieved. Thus, for example, the score of the initial virtual dental model 100 illustrated in FIG. 1A is "5," relative to an ideal case having a score of "0."

Figure 1B:
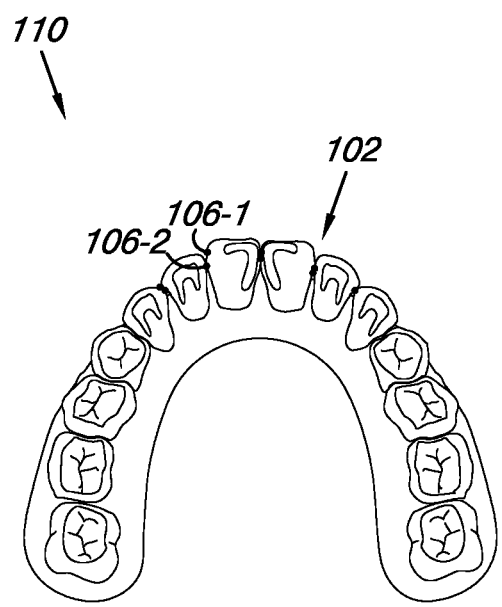
FIG. 1B illustrates a treatment outcome virtual dental model corresponding to the initial virtual dental model illustrated in FIG. 1A having dental references assigned thereto according to a prior art method.

FIG. 1B illustrates a treatment outcome virtual dental model corresponding to the initial virtual dental model illustrated in FIG. 1A having dental references assigned thereto according to a prior art method. The treatment professional can use his best judgment to assign the dental references 102 to the treatment outcome virtual dental model 110 with reference to the dental references 102 assigned to the initial virtual dental model 100. That is, for each dental reference 102 assigned to the initial virtual dental model 100, the treatment professional can attempt to assign a dental reference 102 to the treatment outcome virtual dental model 110 at the same point or points.

For example, the treatment professional can attempt to assign contact points 106-1 and 106-2 to the treatment outcome virtual dental model 110 at the exact same locations on the respective teeth as the contact points 104-1 and 104-2 assigned to the initial virtual dental model 100. However, as the reader will appreciate, there will be some noise in the data corresponding to the assigned points due to inaccuracy in the assignment. The scorer may choose a location in the outcome model corresponding to a similar point identified in the initial model, which may not necessarily be the exact same location for that point as that identified in the initial model.

The accuracy of such prior art methods relies on the treatment professional's ability to pick the exact same points among various virtual dental models and to pick the "correct points," (e.g., contact points 106-1 and 106-2) assuming such points exist. Furthermore, the score is based on a pre-determined absolute scale to which the initial 100 and treatment outcome 110 virtual dental models are compared. As described herein, in many cases the "ideal" cannot be achieved, such as in some cases of primary dentition, mixed dentition, worn dentition, pre-restoration, extensive restoration, limited treatment, lower incisor extraction, tooth-size discrepancy, and the like.

Thus, for example, the score of the treatment outcome virtual dental model 110 illustrated in FIG. 1B can be 1.6. As compared to the score of the initial virtual dental model 100 illustrated in FIG. 1A, a 68% improvement has been achieved according to this scoring system. That is, 5−1.6=3.4, where 5 represents a score of the initial virtual dental model 100 and 1.6 represents the score of the treatment outcome virtual dental model 110. 3.4÷5=0.68, where 0.68 represents the fraction of improvement achieved toward an ideal condition. Thus, the 68% improvement may seem to indicate a rather poor treatment outcome. However, the score provided by such prior art methods is relative to a notion of an "ideal," and does not take into account whether that "ideal" can be realistically achieved.

Additional complications of some prior art approaches include dental references that are broad surface areas rather than singular points. The potential for multiple singular points to exist within a broad surface area for such types of dental references may lead to variability in the determination of the reference, particularly among different virtual dental models (e.g., at different stages of treatment).

Furthermore, such prior art scoring systems can yield variability issues between different treatment professionals who may apply the scoring systems differently and/or assign dental references differently, etc. For example, consider two hypothetical patients having the exact same dental conditions and who are treated by two different professionals and achieve the exact same physical treatment outcome. Based on the abilities of the two treatment professionals to use the prior art scoring systems, different treatment index scores may result although the actual physical outcome of treatment was exactly the same for both patients. This is known as inter-operator variability. While calibration between operators can reduce the variability, it is generally not eliminated.

Figure 2A:
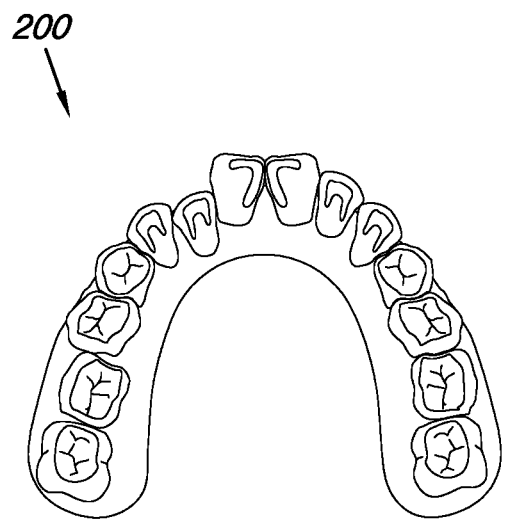
FIG. 2A illustrates an initial virtual dental model according to one or more embodiments of the present disclosure.

FIG. 2A illustrates an initial virtual dental model according to one or more embodiments of the present disclosure. As described herein, the initial virtual dental model 200 can be obtained from a first scan of a patient's dentition prior to treatment or at an intermediate state of treatment (e.g., before treatment has been completed). Rather than assigning dental references to the initial virtual dental model 200, one or more embodiments of the present disclosure first define a specific treatment goal and use a target virtual dental model based on that treatment goal.

Figure 2B:
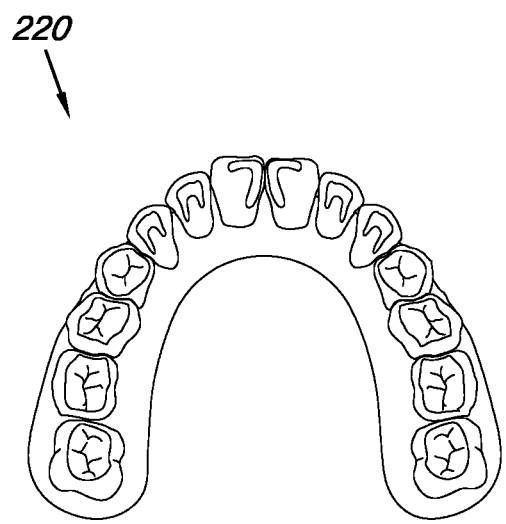
FIG. 2B illustrates a target virtual dental model corresponding to the initial virtual dental model illustrated in FIG. 2A according to the present disclosure.

FIG. 2B illustrates a target virtual dental model corresponding to the initial virtual dental model illustrated in FIG. 2A according to the present disclosure. The target virtual dental model 220 can be created by modifying the initial virtual dental model 200 according to one or more treatment goals. One example of creating a target virtual dental model is described in U.S. Pat. No. 7,134,874 to Chisti et al., which is assigned to Align Technology, Inc.

The one or more treatment goals are case-specific (e.g., specific to the particular patient on which the initial virtual dental 200 model was based). Because the one or more treatment goals are case-specific, the target virtual dental model 220 can apply to cases that could not be accurately scored by prior art treatment indices such as mixed dentition, primary dentition, restored/worn dentition, missing teeth dentition, tooth-size discrepancy dentition, pre-restorative dentition, and the like.

Thus, the target virtual dental model 220 illustrated in FIG. 2B represents a modification of the initial virtual dental model 200 illustrated in FIG. 2A according to one or more treatment goals defined by a treatment professional associated with the patient. The target virtual dental model 220 does not have to correspond to an "ideal" treatment outcome as described herein (e.g., a generic ideal dentition that does correspond to any particular patient). The target virtual dental model 220 represents the treatment professional's opinion as to the best outcome for the particular patient that can reasonably be achieved with the orthodontic treatment methods available to the treatment professional. That is, a standard against which to measure the "quality" of the actual treatment outcome for the particular patient has been defined in advance by the treatment professional with the target virtual dental model 220.

Figure 2C:
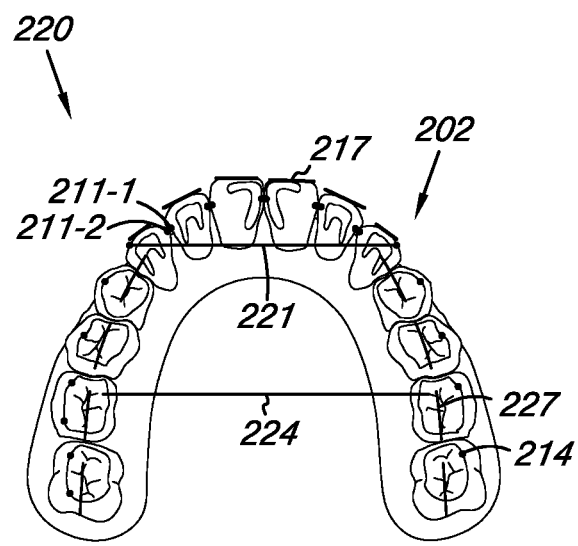
FIG. 2C illustrates the target virtual dental model illustrated in FIG. 2B having dental references assigned thereto according to one or more embodiments of the present disclosure.

FIG. 2C illustrates the target virtual dental model illustrated in FIG. 2B having dental references assigned thereto according to one or more embodiments of the present disclosure. In contrast to some prior art methods, dental references 202 in the embodiment illustrated in FIG. 2A-2D are first assigned to a target virtual dental model 220 (e.g., instead of to the existing condition).

One of ordinary skill in the art will appreciate the various dental references that can be assigned, such as, contact points 211-1 and 211-2 between teeth, cusp tips 214, facial lines 217, cuspid width 221, and molar width 224, among others. Contact points such as contact points 211-1 and 211-2 can be used for determination of alignment, cusp tip points 214 can be used for determination of arch length, cuspid width 221 and molar width 224 can be used for a determination of arch width, facial lines 217 can be used for determination of arch curve, and facial aspect of clinical crown (FACC) lines (not shown) can be used for determination of angulation and inclination. FACC can be a subset of facial lines. Any line on the facial surface of the tooth could be considered to be a facial line (e.g., including horizontal references).

According to the present disclosure, the dental references 202 are assigned to the target virtual dental model 220 based on the treatment professional's judgment of a specific target outcome, as opposed to the dental references 202 being assigned to "idealized" locations based on a generic "ideal" case that may be unachievable. Such embodiments, allow the treatment professional to pinpoint a more accurate, if not exact, location for the dental references 202 on the target virtual dental model.

The location of the dental references 202 assigned to the target virtual dental model 220 by the treatment professional can be assigned in an algorithmically determined fashion. Dental references 202 can be used to define "good" alignment for a treatment outcome (e.g., if corresponding dental references on the patient's treatment outcome virtual model 210 (e.g., as illustrated in FIG. 2E) match the dental references 202 on the target virtual dental model 220, then "good" alignment has been achieved). The dental references 202 on the target virtual dental model 220 can serve as references from which to measure differences in an initial virtual dental model 200 and/or a treatment outcome virtual dental model 210 (e.g., in order to evaluate the patient's initial condition and/or the progress/actual treatment outcome).

As such, a score can be calculated for the target virtual dental model 220. The score can be calculated using any of a number of available scoring systems such as those described herein, or some other scoring system. However, contrary to prior art methods, both the patient's initial condition and treatment outcome are scored against a defined target (e.g., treatment outcome goal) that is individualized to the patient, according to the context of the established target as determined by the treatment professional, as opposed to being scored against an idealized generic goal that may be an inappropriate basis of comparison for the particular patient being evaluated (e.g., using an adult dentition definition of "ideal" as a basis to score a child's dentition). For example, the target virtual dental model 220 can have a score of 1 (e.g., representing a less than "ideal" target outcome, as opposed to a score of 0 for an "ideal" outcome).

Figure 2D:
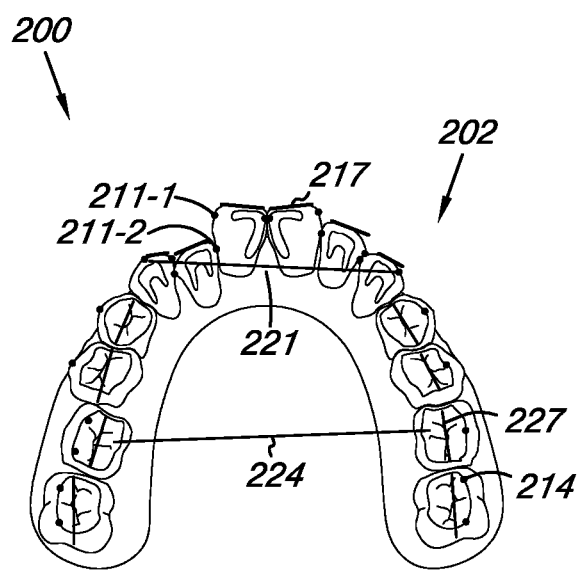
FIG. 2D illustrates the initial virtual dental model illustrated in FIG. 2A having the dental references assigned to the target virtual dental model illustrated in FIG. 2B mapped thereto according to one or more embodiments of the present disclosure.
Figure 2E:
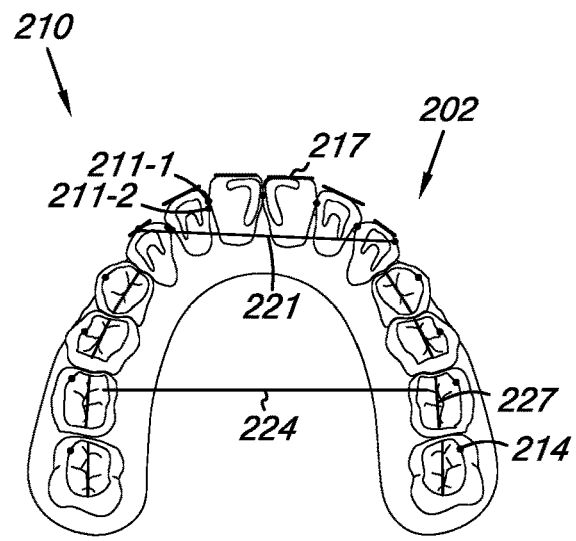
FIG. 2E illustrates a treatment outcome virtual dental model having the dental references assigned to the target virtual dental model illustrated in FIG. 2B mapped thereto according to one or more embodiments of the present disclosure.

FIG. 2D illustrates the initial virtual dental model illustrated in FIG. 2A having the dental references assigned to the target virtual dental model illustrated in FIG. 2B mapped thereto according to one or more embodiments of the present disclosure. The dental references 202 from the target virtual dental model 220 can be mapped to the initial virtual dental model 200. Because the dental references 202 can be mapped (e.g., by computing device implemented superimpositions of the dental references 202), the dental references 202 illustrated on the initial virtual dental model 200 represent the exact same references (e.g., points) on the virtual teeth, although the orientation (e.g., the special positions) of the references may change with the changed orientation of the teeth relative to the target virtual dental model 220. The references can be in the same position on the respective teeth, but since the teeth may be in a different position due to the administered treatment, the position of a particular reference in space may be different.

The dental references 202 can be used to determine an amount of discrepancy between the initial virtual dental model 200 and the target virtual dental model 220. Similarly, a discrepancy between the outcome model 210 and an intermediate outcome model (not specifically illustrated) may also be calculated. A score can be calculated for the initial virtual dental model 200 and compared to the target virtual dental model 220 based at least in part on the special orientation differences between the dental references 202. As described above, the score can be calculated using any of a number of scoring systems. For example, the initial virtual dental model 200 can have a score of 6.

FIG. 2E illustrates a treatment outcome virtual dental model having the dental references assigned to the target virtual dental model illustrated in FIG. 2B mapped thereto according to one or more embodiments of the present disclosure. The treatment outcome virtual dental model 210 can be received from a second scan of the patient's dentition (e.g., a scan at the completion of treatment or at some point during treatment after the first scan). The dental references 202 can be mapped from the target virtual dental model 220 to the treatment outcome virtual dental model 210.

Assigning dental references 202 to the target virtual model 220 and then mapping the dental references 202 to the treatment outcome virtual model 210 can help reduce and/or eliminate inaccuracy (e.g., noise) associated with assignment of dental references to models corresponding to different points during treatment according to some prior art methods at least in part. Such inaccuracy can be reduced due, at least in part, to the accuracy of mapping algorithms as compared to dental reference transfers between various models performed manually by the treatment professional.

Mapping the dental references 202 from the target virtual dental model 220 to the initial virtual dental model 200 and/or the treatment outcome virtual dental model 210 can include the use of one or more algorithms including a transformation algorithm and/or a shrink-wrap algorithm. For example, a transformation algorithm can transform individual dental references 202 from a coordinate system associated with the target virtual dental model 220 to a coordinate system associated with the initial 200 and/or treatment outcome 210 virtual dental models. For example, a shrink-wrap algorithm can adjust coordinates of a particular dental reference in cases where the target virtual dental model 220 has a scale that differs from the initial 200 and/or treatment outcome 210 virtual dental models.

The dental references 202 can be used to determine an amount of discrepancy between the treatment outcome virtual dental model 210 and the target virtual dental model 220. A score can be calculated for the treatment outcome virtual dental model 210 and compared to the target virtual dental model 220 based at least in part on the discrepancies between corresponding dental references 202. As described above, the score can be calculated using any of a number of scoring systems. For example, the treatment outcome virtual dental model 210 can have a score of 1.3.

Using the scores calculated for the target virtual dental model 220 and the treatment outcome virtual dental model 210, a more meaningful evaluation of the treatment of the patient can be provided. Rather than comparing the patient's treatment outcome to the patient's initial condition within the context of a generic idealized outcome that might not be realistically attainable relative to the patient's initial condition, the patient's treatment outcome can be compared to the patient's initial condition within the context of a treatment goal specifically established by the treatment professional.

Thus, using the example scored given in the discussion above, a 94% improvement has been achieved according to this scoring system. That is, 6−1=5, where 6 represents a score of the patient's initial condition, 1 represents a score of the patient's target outcome condition, and 5 represents a score characterizing the total improvement that is determined to be the target appropriate for the patient. 6−1.3=4.7, where 1.3 represents a score of the patient's actual treatment outcome condition and 4.7 represents a score characterizing the total improvement actually achieved relative to the target goal. 4.7÷5=0.94, where 0.94 represents the fraction of possible improvement achieved based on the actual treatment outcome. This scoring can be contrasted with some previous approaches, which would assign a score of 0 to an ideal outcome and would rate this example case as only a 78% improvement (4.7÷6=0.78) despite a good outcome relative to the intended objective.

The individualized orthodontic treatment index scoring system described herein is advantageous over those previous approaches that relate outcome scores to the concept of an ideal goal rather than to a patient-specific, treatment professional defined goal because the scoring system yields a score that meaningfully characterizes treatment outcomes across all types of initial patient conditions. Prior art scoring systems can yield disproportionately positive results for patients having more "normal" initial conditions and disproportionately negative results for patients having more "abnormal" initial conditions. Such prior art systems can prevent patients who do not fit the norm from receiving an accurate assessment of their treatment outcomes, as their initial condition is inherently biased toward lower scores as a result of their disqualification from possibly achieving an ideal score.

Using the individualized orthodontic treatment index scoring system according to one or more embodiments of the present disclosure can allow for a more accurate assessment of "good" or "acceptable" scores and "bad" or "unacceptable" scores for many different types of initial patient conditions and not just for permanent non-restored adult teeth where no tooth-size discrepancy exists. Such scoring zones can be established for primary teeth, mixed dentition, significantly restored and/or occlusally worn teeth, pre-restorative set-ups, tooth-size discrepancy (even specific teeth of tooth-size discrepancy such as prior incisor extraction), limited treatment, and/or ideal conditions. Thus, the individualized orthodontic treatment index provides a contextually objective method of scoring orthodontic treatment.

An accumulation of retrospective data (e.g., in a database), such as the frequency of different types of initial patient conditions along with a corresponding treatment professional's preferred treatment objectives, would allow a correlation to be established between the individualized orthodontic treatment index and a predictability of a desired index outcome for future cases. Such correlation can be established as a predictability index.

Figure 3:
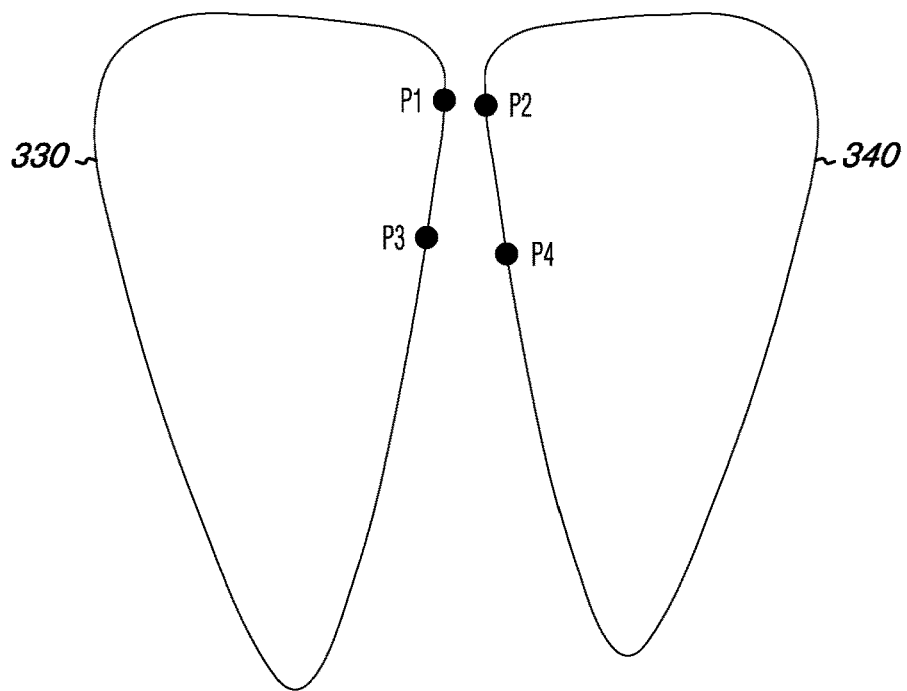
FIG. 3 illustrates an interproximation relationship between two spaced teeth according to one or more embodiments of the present disclosure.
Figure 4:
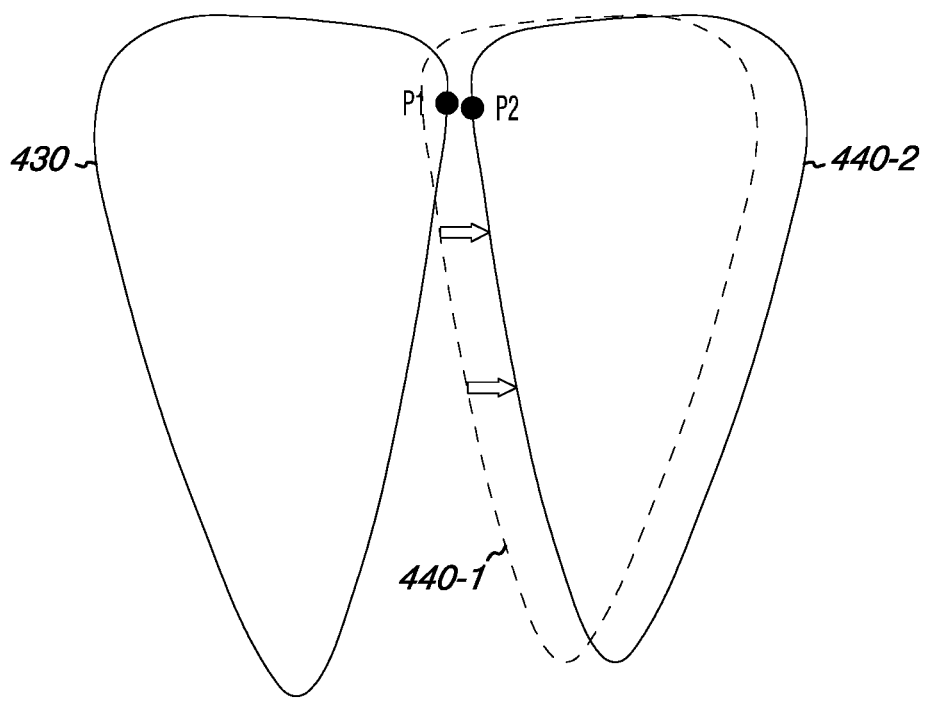
FIG. 4 illustrates an interproximation relationship between two overlapped teeth according to one or more embodiments of the present disclosure.
Figure 5:
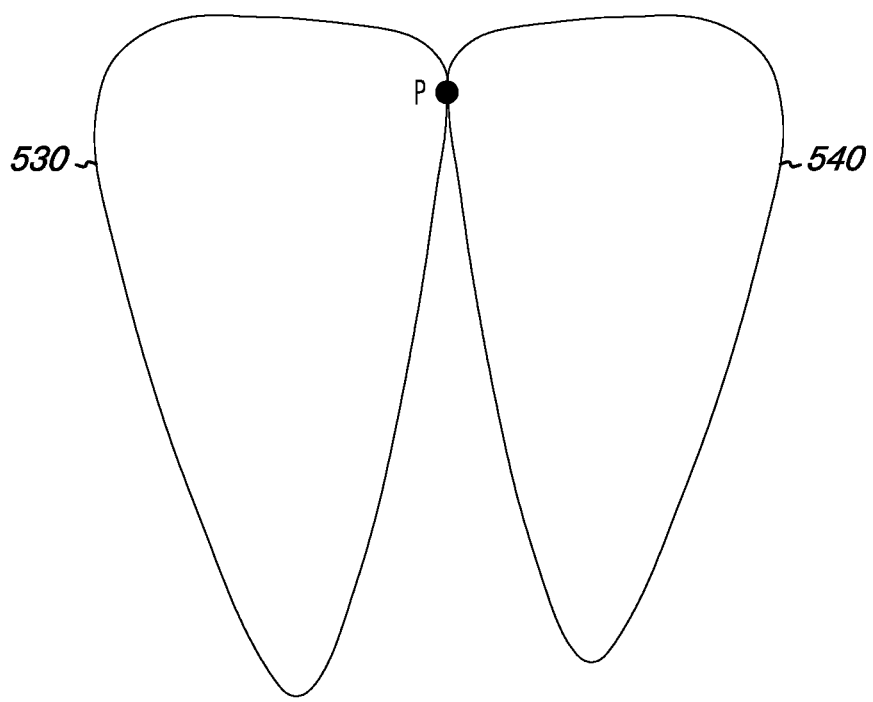
FIG. 5 illustrates an interproximation relationship between two point-contacted teeth according to one or more embodiments of the present disclosure.

As described herein, one example of a dental reference is a contact relationship between adjacent teeth based on a difference between contact points on individual teeth. FIGS. 3-5 illustrate different interproximation relationships between adjacent teeth. While an "ideal" treatment outcome may result in a point-contacted interproximation relationship (e.g., a single point of contact, P, as illustrated in FIG. 5) for all adjacent teeth, some patients may not have such a relationship as a realistic treatment goal for all of their adjacent tooth pairs.

For example, in a limited treatment, the goal may be to only treat the anterior teeth, without any treatment to the posterior teeth, which may contain one or more discrepancies in the contact relationships. Under a scoring system based on an ideal score, the impact of any achieved treatment outcome will be diluted to an extent by the discrepancies that exist in the areas not being treated. Accordingly, one or more embodiments of the present disclosure can assign dental references to a target virtual dental model having one or more virtual teeth that are not in an "ideal" configuration. According to one or more embodiments of the present disclosure, limited treatment cases can be evaluated to provide further insight as to whether a reported index is in line with the best practices of treatment professionals.

FIG. 3 illustrates an interproximation relationship between two spaced virtual teeth according to one or more embodiments of the present disclosure. A first tooth 330 and a second tooth 340 in a target virtual dental model may be spaced apart from one another. In such a scenario, a single contact point does not exist between the first tooth 330 and the second tooth 340. In cases where specific amounts of space are actually desirable as part of the treatment outcome (e.g., pre-restorative set-ups, set-ups where idiosyncratic familial characteristics are intended to be preserved), whether the desired outcome is successfully achieved can be accurately measured according to the present disclosure, whereas under the prior art systems, the success of this kind of treatment goal would not be accurately assessed.

Accordingly, an algorithm can detect the two closest points (P1 and P2) between the first tooth 330 and the second tooth 340 on the surfaces thereof. The two closest points (P1 and P2) can be respective points on each tooth with a minimum distance therebetween. That is, the two closest points (P1 and P2) have a distance therebetween that is less than a combination of any other two points (e.g., points P3 and P4) on the first tooth 330 and the second tooth 340.

An algorithm can detect points P1 and P2 automatically and assign the pair as dental references for the first tooth 330 and the second tooth 340 in the target virtual dental model. Such an algorithm can be used when a particular pair of adjacent virtual teeth on the target virtual dental model are spaced apart. As one of ordinary skill in the art will appreciate, spacing between adjacent teeth can be a component of an orthodontic treatment index score.

FIG. 4 illustrates an interproximation relationship between two overlapped virtual teeth according to one or more embodiments of the present disclosure. A first tooth 430 and a second tooth 440-1 in a target virtual dental model may be overlapped. In such a scenario, a single contact point does not exist between the first tooth 430 and the second tooth 440-1 because multiple contact points exist.

With respect to FIG. 4, the dotted outline of the second virtual tooth 440-1 indicates the position of the second tooth 440-1 in the treatment outcome virtual dental model. The solid outline of the second tooth 440-2 indicates a translation of the position of the second tooth as described herein.

An algorithm can compute such a translation to separate the first tooth 430 and the second tooth 440-2 by a very small space (e.g., 0.01 millimeters). Such a translation can be calculated as a translation that separates the first tooth 430 and the second tooth 440-2 by a minimum amount as compared to other translations.

Subsequent to the calculation and application of the translation, contact points (P1 and P2) for the first tooth 430 and the second tooth 440-2 can be calculated as described above with respect to FIG. 3. For calculating contact points, other methods may be used, including collision detection methods such as axis-aligned bounding boxes (AABB) tree and oriented bounding boxes (OBB) tree based collision detections. An OBB is a rectangular bounding box at an arbitrary orientation in 3D space. A collection of OBBs can be referred to as an OBB tree. An AABB is a rectangular bounding box constrained by edges parallel to coordinate axes. A collection of AABBs can be referred to as an AABB tree.

FIG. 5 illustrates an interproximation relationship between two point-contacted virtual teeth according to one or more embodiments of the present disclosure. A first tooth 530 and a second tooth 540 in a target virtual dental model may have a single point of contact. In such a scenario, the single contact point (P) can be used directly as a dental reference. The single contact point P can be assigned as one point, common to the first tooth 530 and the second tooth 540. The single contact point (P) can be assigned as two points (having the same coordinates if a common coordinate system is shared between the first tooth 530 and the second tooth 540), one on each tooth.

One or more embodiments of the present disclosure can employ other methods of assigning dental references to a target virtual dental model having one or more virtual teeth that are not in an "ideal" configuration. For example, typodont tooth morphing can be used to assign dental references to a target virtual dental model by morphing corresponding references from a virtual typodont (e.g., using a reference library of idealized tooth shapes).

As used herein a typodont refers to a virtual dental model including a number of ideal tooth shapes (e.g., from a reference library of idealized tooth shapes). Dental references (e.g., contact points) can be assigned to the typodont. Then, landmarks can be created on the typodont and corresponding landmarks can be created on the target virtual dental model. Additional discussion of a reference library of idealized tooth shapes can be found in U.S. patent application Ser. No. 11/888,742 entitled "Mapping Abnormal Dental References" filed Aug. 2, 2007, having at least one common inventor and assigned to Align Technology, Inc.

Such embodiments may be particularly useful for virtual teeth that have incomplete crows (e.g., representative of a chipped tooth, a partially erupted tooth, etc.). For example, a treatment professional may wish to use a cusp tip as a dental reference on a tooth that is chipped such that the tip is missing from the target virtual dental model. In such an example, the dental reference could be assigned to a typodont and then morphed from the typodont to the target virtual dental model to best approximate where the cusp tip should be located relative to the existing flat surface.

Based on the landmarks, a morphing function can be calculated for morphing from the typodont to the target virtual dental model. The morphing function can be applied to the dental references assigned to the typodont to obtain corresponding dental references on the target virtual dental model. Once dental references for the target virtual dental model have been obtained (e.g., assigned), an individualized orthodontic treatment index scoring system can operate as described herein.

In some embodiments, thin-plate spline based mapping can be used with respect to calculating a morphing function using the landmarks. Use of such a thin-plate spline may minimize the deformation energy effects (e.g., minimize the degree or extent of bend in the resulting surface between created landmarks). The deformation energy can be defined as:

$$\int\int_{R^2}\left(\frac{\partial^2 f}{\partial^2 x^2}\right)^2 + 2\left(\frac{\partial^2 f}{\partial x \partial y}\right)^2 + \left(\frac{\partial^2 f}{\partial^2 y^2}\right)^2 dxdy$$

Once the morphing function is calculated, it may be applied to the dental references assigned to the typodont to morph the same to the target virtual dental model. Additional discussion of typodont virtual models and morphing functions is described in U.S. patent application Ser. No. 11/951,812 entitled "System and Method for Improved Dental Geometry Representation" filed Dec. 6, 2007 having at least one common inventor with the present application, and assigned to Align Technology, Inc.

One or more embodiments of the present disclosure can include mapping dental references from a target virtual dental model to a treatment outcome virtual dental model and/or an initial virtual dental model. Mapping dental reference points can include calculating a matching transform from the target virtual dental model (the entire model, and individual tooth therein, and/or one or more points therein) to the treatment outcome virtual dental model and/or initial virtual dental model. For example, an iterative closest point (ICP) algorithm can be used to calculate the matching transform.

An ICP algorithm can minimize the differences between two point clouds (e.g., between the target virtual dental model and the treatment outcome virtual dental model and/or the initial virtual dental model). The ICP algorithm can iteratively associate points between the two virtual dental models, estimate transformation parameters using a mean square cost function, and transform points from the first virtual dental model to the second virtual dental model using the estimated parameters. Such iteration can continue until the change in mean square error falls within a particular threshold. In some embodiments, a particular number of iterations can be selected rather than using a threshold limit in order to avoid slower processing times that may be associated with later iterations that converge on a local minimum.

Once the transform has been calculated it can be applied to a dental reference (e.g., a contact point) from the target virtual dental model to transform the dental reference to a corresponding dental reference on the treatment outcome virtual dental model and/or initial virtual dental model. The corresponding dental reference can be used as-calculated from the transform and/or the corresponding dental reference can be projected onto the surface of the treatment outcome virtual dental model and/or initial virtual dental model.

Examples of the calculation of transforms and projections for 3-D dental modeling applications are provided in U.S. patent application Ser. No. 12/583,479 entitled "Digital Dental Modeling" filed Aug. 21, 2009, having at least one common inventor with the present application, and assigned to Align Technology, Inc.

Figure 6:
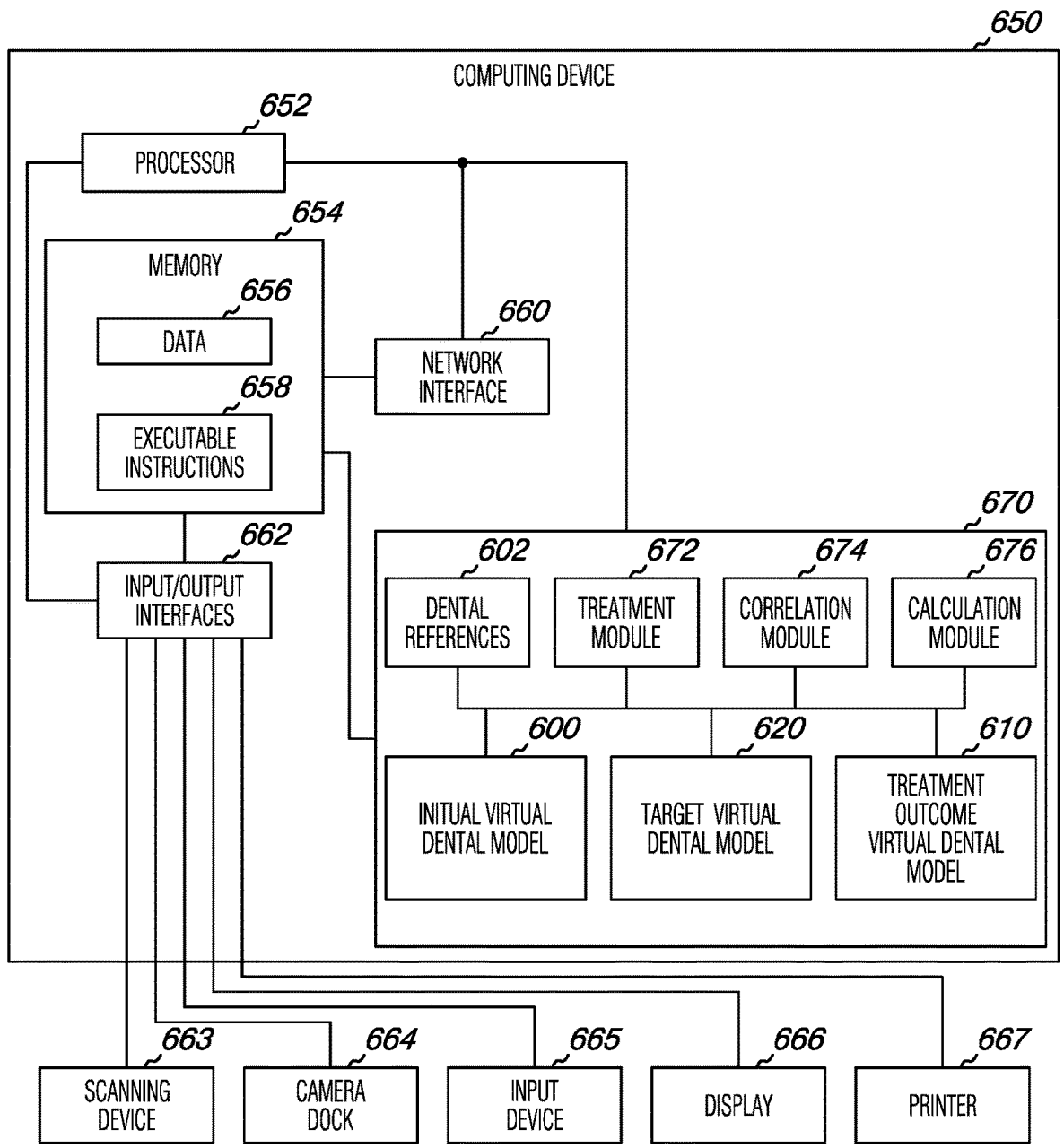
FIG. 6 illustrates a system for using an individualized orthodontic treatment index according to one or more embodiments of the present disclosure.

FIG. 6 illustrates a system for using an individualized orthodontic treatment index according to one or more embodiments of the present disclosure. In the system illustrated in FIG. 6, the system includes a computing device 650 having a number of components coupled thereto. The computing device 650 includes a processor 652 and memory 654. The memory can include various types of information including data 656 and executable instructions 658 as discussed herein.

Memory and/or the processor may be located on the computing device 650 or off the device in some embodiments. As such, as illustrated in the embodiment of FIG. 6, a system can include a network interface 660. Such an interface can allow for processing on another networked computing device or such devices can be used to obtain information about the patient or executable instructions for use with various embodiments provided herein.

As illustrated in the embodiment of FIG. 6, a system can include one or more input and/or output interfaces 662. Such interfaces can be used to connect the computing device with one or more input or output devices.

For example, in the embodiment illustrated in FIG. 6, the system can include connectivity to a scanning device 663, a camera dock 664, an input device 665 (e.g., a keyboard, mouse, etc.), a display device 666 (e.g., a monitor), a printer 667, and one or more other input devices 665. The input/output interface 662 can receive data, storable in the data storage device (e.g., memory 654), representing the digital dental model corresponding to the patient's upper jaw and the patient's lower jaw.

In some embodiments, the scanning device 663 can be configured to scan one or more physical molds of a patient's dentition. In one or more embodiments, the scanning device 663 can be configured to scan the patient's dentition directly. The scanning device 663 can be configured to input data to the application modules 670.

The camera dock 664 can receive an input from an imaging device (e.g., a two-dimensional imaging device) such as a digital camera or a printed photograph scanner. The input from the imaging device can be stored in the data storage device (e.g., memory 654).

The processor 652 can be configured to provide a visual indication of a virtual dental model on the display 666 (e.g., on a GUI running on the processor 652 and visible on the display 666). The GUI can be configured to allow a treatment professional to input treatment goals and/or to create a target virtual dental model 620. The GUI can be configured to allow a treatment professional to select and/or mark one or more dental references 602 on a virtual dental model (e.g., an initial virtual dental model 600, a target virtual dental model 620 and/or a treatment outcome virtual dental model 610). Input received via the GUI can be sent to the processor 652 as data and/or can be stored in memory 654.

Such connectivity can allow for the input and/or output of data and/or instructions among other types of information. Although some embodiments may be distributed among various computing devices within one or more networks, such systems as illustrated in FIG. 6 can be beneficial in allowing for the capture, calculation, and/or analysis of information discussed herein.

The processor 652, in association with the data storage device (e.g., memory 654), can be associated with data and/or application modules 670. The processor 652, in association with the memory 654, can store and/or utilize data and/or execute instructions to provide a number of application modules for using an individualized orthodontic treatment index.

Such data can include the initial virtual dental model 600, the target virtual dental model 620, and/or the treatment outcome virtual dental model 610. The initial virtual dental model 600 can be derived from a first scan of a patient's dentition and the treatment outcome virtual dental model 610 can be derived from a second (e.g., later) scan of the patient's dentition. The target virtual dental model 620 can include a number of dental references 602 assigned thereto.

Such application modules can include a treatment module 672, a correlation module 674, and/or a calculation module 676. The treatment module 672 can be configured to create the target virtual dental model 620 by modifying the initial virtual dental model 600 based on a treatment goal (e.g., a treatment goal specified by a treatment professional). The correlation module 674 can be configured to map a number of dental references 602 from the target virtual dental model 620 to the initial virtual dental model 600 and to the treatment outcome virtual dental model 610.

The calculation module 676 can be configured to calculate an individualized treatment index score for the treatment outcome virtual dental model 610 according to one or more differences between the target virtual dental model 620 and the treatment outcome virtual dental model 610 based on the number of dental references 602. For example, when the dental references 602 include contact points of anterior teeth, the calculation module 676 can be configured to calculate an alignment deviation of the patient's dentition based on the contact points of anterior teeth. When the dental references 602 include cusp tip points, the calculation module can be configured to calculate an arch length of the patient's dentition based on the cusp tip points.

When the dental references 602 include cuspid and molar widths, the calculation module can be configured to calculate an arch width of the patient's dentition based on the cuspid and the molar widths. When the dental references 602 include facial lines, the calculation module can be configured to calculate an arch curve of the patient's dentition based on the facial lines. When the dental references 602 include FACC lines, the calculation module can be configured to calculate an angulation and an inclination of the patient's dentition based on the FACC lines.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A method of digital orthodontic treatment planning using a graphical user interface, the method comprising:

receiving an initial virtual dental model, the initial virtual dental model including first data from a first scan of a patient's dentition, the initial virtual dental model representing the patient's dentition at a first stage of an orthodontic treatment plan, the initial virtual dental model associated with a first score;

generating a target virtual dental model by virtually modifying the initial virtual dental model, the target virtual dental model representing a target outcome of a limited treatment for the patient's dentition, wherein generating the target virtual dental model includes graphically assigning dental references on the target virtual dental model, wherein at least one of the dental references is assigned by morphing a corresponding at least one dental reference from a virtual typodont having at an ideal configuration, wherein the target virtual dental model is associated with a second score that is different than the first score, wherein graphically assigning the dental references includes:

assigning contact points to two adjacent teeth that are overlapped based on detecting a collision between the two adjacent teeth using axis-aligned bounding boxes (AABB) tree detection, wherein the AABB tree detection includes using a rectangular bounding box constrained by edges parallel to coordinate axes;

calculating and applying a translation for one of the two adjacent teeth as applied to the one of the two adjacent teeth, wherein the translation minimally separates the two adjacent teeth; and using the contact points to model an interproximal relationship characterizing the limited treatment;

mapping the dental references assigned to the target virtual dental model to a treatment outcome virtual dental model, the treatment outcome virtual dental model including second data from a second scan of the patient's dentition, the treatment outcome virtual dental model representing an actual outcome during or after implementing the limited treatment for the patient's dentition, the treatment outcome virtual dental model associated with a third score that is different than each of the first and second scores;

comparing differences between the target virtual dental model and the treatment outcome virtual dental model;

determining an individualized treatment index score for the treatment outcome virtual dental model based on the comparison between the target virtual dental model and the treatment outcome virtual dental model, wherein determining the individualized treatment index score comprises determining a target improvement calculated using the second and third scores; and providing an evaluation of the treatment of the patient's dentition using the individualized treatment index score calculated for the target virtual dental model and the treatment outcome virtual dental model.

2. The method of claim 1, further comprising:
mapping first locations of dental references from the target virtual dental model to third locations on the initial virtual dental model;
comparing the first locations of dental references of the target virtual dental model and the third locations to identify second differences between the target virtual dental model and the initial virtual dental model; and
determining a second individualized treatment index score for the initial virtual dental model using the second differences.

3. The method of claim 2, further comprising:
comparing the individualized treatment index score and the second individualized treatment index score; and
determining an improvement of the treatment outcome virtual dental model relative to the target virtual dental model, the improvement based on the comparison of the individualized treatment index score and the second individualized treatment index score.

4. The method of claim 1, wherein comparing the differences between the target virtual dental model and the treatment outcome virtual dental model includes:
calculating a matching transform from at least a portion of the target virtual dental model to at least a corresponding portion of the treatment outcome virtual dental model; and
applying the matching transform to dental references of the target virtual dental model and the treatment outcome virtual dental model.

5. The method of claim 4, further comprising comparing first locations of dental references of the target virtual dental model and second locations of the treatment outcome virtual dental model by projecting at least one dental reference from the at least the portion of the target virtual dental model to the at least the corresponding portion of the treatment outcome virtual dental model.

6. The method of claim 1, wherein the target virtual dental model includes a space between adjacent teeth or an overlap of adjacent teeth, wherein the teeth in ideal configuration does not include a space between corresponding adjacent teeth or an overlap of corresponding adjacent teeth.

7. The method of claim 1, wherein the limited treatment includes modifying a contact relationship between adjacent anterior teeth without modifying a contact relationship between adjacent posterior teeth.

8. The method of claim 1, wherein the target virtual dental model includes at least one pair of adjacent teeth that does not have a single point of contact.

9. The method of claim 1,
wherein comparing the differences between the target virtual dental model and the treatment outcome virtual dental model comprises comparing first locations where dental references reside on the target virtual dentition model to second locations where dental references reside on the treatment outcome virtual dentition model.

10. The method of claim 9, wherein the dental references include: closest points on adjacent teeth, contact points between adjacent teeth, or closest points on adjacent teeth and contact points between adjacent teeth.

11. The method of claim 1, wherein the virtual typodont is based on a reference library of ideal virtual teeth.

12. A non-transitory computing device readable medium having executable instructions executed by a processor to cause a computing device to perform a method of digital orthodontic treatment planning using a graphical user interface, the method comprising:
receiving an initial virtual dental model, the initial virtual dental model including first data from a first scan of a patient's dentition before or during an orthodontic treatment plan, the initial virtual dental model associated with a first score;
generating a target virtual dental model by virtually modifying the initial virtual dental model according to a limited treatment of the orthodontic treatment plan, wherein generating the target virtual dental model includes graphically assigning dental references on the target virtual dental model, wherein at least one of the dental references is assigned by morphing a corresponding at least one dental reference from a virtual typodont having at an ideal configuration, wherein the target virtual dental model associated with a second score that is different than the first score, wherein graphically assigning the dental references includes:
assigning contact points to two adjacent teeth that are overlapped based on detecting a collision between the two adjacent teeth using axis-aligned bounding boxes (AABB) tree detection, wherein the AABB tree detection includes using a rectangular bounding box constrained by edges parallel to coordinate axes;
calculating and applying a translation for one of the two adjacent teeth as applied to the one of the two adjacent teeth, wherein the translation minimally separates the two adjacent teeth; and
using the contact points to model an interproximal relationship characterizing the limited treatment;
mapping the dental references assigned to the target virtual dental model to a treatment outcome virtual dental model, the treatment outcome virtual dental model including second data from a second scan of the patient's dentition during or after the orthodontic treatment plan, the treatment outcome virtual dental model representing an actual outcome of the orthodontic treatment plan, the treatment outcome virtual dental model associated with a third score that is different than each of the first and second scores;
comparing differences between the target virtual dental model and the treatment outcome virtual dental model;
determining an individualized treatment index score that characterizes the treatment outcome virtual dental model based on the comparison between the target virtual dental model and the treatment outcome virtual dental model, wherein determining the individualized treatment index score comprises determining a target improvement calculated using the second and third scores; and
providing an evaluation of the treatment of the patient's dentition using the individualized treatment index score calculated for the target virtual dental model and the treatment outcome virtual dental model.

13. The medium of claim 12, further comprising assigning the dental references to the target virtual dental model by:
assigning contact points to two adjacent teeth represented in the target virtual dental model, the two adjacent teeth having a space there between; and
using the contact points to model an interproximal relationship characterizing the limited treatment.

14. The medium of claim 12, wherein assigning the contact points includes using oriented bounding box (OBB) tree based collision detection.

15. The medium of claim 12, further comprising assigning the dental references to the target virtual dental model by assigning contact points to two adjacent teeth that contact at a single point.

16. The medium of claim 12, wherein morphing the corresponding at least one dental reference from the virtual typodont comprises:
calculating a morphing function from the virtual typodont to a corresponding tooth to the target virtual dental model; and
applying to the morphing function to a reference point on the virtual typodont to assign the reference point to a corresponding tooth of the target virtual dental model.

17. The medium of claim 16, wherein applying the morphing function includes using thin-plate spline based mapping to minimize an energy of a surface deformation associated with the morphing function.

18. The medium of claim 12, wherein mapping the dental references from the target virtual dental model to the treatment outcome virtual dental model comprises:
calculating a transform from a tooth of the target virtual dental model to a corresponding tooth of the treatment outcome virtual dental model; and
applying the transform to dental references associated with the tooth of the target virtual dental model to transform the dental references from the tooth of the target virtual dental model to the corresponding tooth of the treatment outcome virtual dental model.

19. The method of claim 18, wherein calculating the transform includes using an iterative closest point (ICP) algorithm.

20. The method of claim 18, wherein mapping the dental references from the target virtual dental model to the treatment outcome virtual dental model further includes projecting the transformed dental references to the corresponding tooth of the treatment outcome virtual dental model.

21. The method of claim 12, wherein generating the target virtual dental model comprises calculating a deviation from the ideal configuration.

22. The method of claim 12, wherein the target virtual dental model includes a first tooth and a second tooth adjacent the first tooth, wherein assigning the dental references to the target virtual dental model comprises:
assigning dental reference points to the target virtual dental model, the dental reference points including a first point on the first tooth and a second point on the second tooth corresponding to the closest points between the first and second teeth of the target virtual dental model, wherein the first point and the second point are separated by a non-zero distance.

23. A system for digital orthodontic treatment planning using a graphical user interface, the system comprising:
a processor; and
a memory storing data, the memory storing instructions executable by the processor to:
create a target virtual dental model by virtually modifying a received initial virtual dental model based on a limited treatment of a dentition, the initial virtual dental model associated with a first score, wherein the limited treatment of the dentition is specific to a patient based on the received initial virtual dental model, and wherein the target virtual dental model is associated with a second score that is different than the first score;
graphically assign dental references to the target virtual dental model, wherein at least one of the dental references is assigned by morphing a corresponding at least one dental reference from a virtual typodont having at an ideal configuration, wherein the morphing includes using thin-plate spline based mapping to minimize an energy of a surface deformation associated with a morphing function from the virtual typodont, and wherein the dental references reside at first locations, the first locations defining features of a target outcome on the target virtual dental model, wherein graphically assigning the dental references includes:
assigning contact points to two adjacent teeth that are overlapped based on detecting a collision between the two adjacent teeth using axis-aligned bounding boxes (AABB) tree detection, wherein the AABB tree detection includes using a rectangular bounding box constrained by edges parallel to coordinate axes;

calculating and applying a translation for one of the two adjacent teeth as applied to the one of the two adjacent teeth, wherein the translation minimally separates the two adjacent teeth; and using the contact points to model an interproximal relationship characterizing the limited treatment;

map the dental references assigned to the target virtual dental model to the initial virtual dental model and to a treatment outcome virtual dental model, the treatment outcome virtual dental model associated with a third score that is different than each of the first and second scores;

calculate an individualized treatment index score for the treatment outcome virtual dental model according to one or more differences between the target virtual dental model and the treatment outcome virtual dental model based on the mapped dental references, wherein calculating the individualized treatment index score comprises determining a target improvement calculated using the second and third scores; and provide an evaluation of the treatment of the patient's dentition using the individualized treatment index score calculated for the target virtual dental model and the treatment outcome virtual dental model.

24. The system of claim 23, wherein the memory further stores instructions executable by the processor to calculate an alignment deviation of the dentition based on the contact points of anterior teeth.

25. The system of claim 23, wherein:
the dental references include cusp tip points; and
the memory further stores instructions executable by the processor to calculate an arch length of the dentition based on the cusp tip points.

26. The system of claim 23, wherein:
the dental references include cuspid and molar widths; and
the memory further stores instructions executable by the processor to calculate an arch width of the dentition based on the cuspid and the molar widths.

27. The system of claim 23, wherein:
the dental references include facial lines; and
the memory further stores instructions executable by the processor to calculate an arch curve of the dentition based on the facial lines.

28. The system of claim 23, wherein:
the dental references include facial aspect of clinical crown (FACC) lines; and
the memory further storing instructions executable by the processor to calculate an angulation and an inclination of the dentition based on the FACC lines.

* * * * *